US012797814B2

(12) United States Patent
Hou et al.

(10) Patent No.: US 12,797,814 B2
(45) Date of Patent: Nov. 17, 2026

(54) SUPPORT AND FT SYNTHESIS CATALYST, AND PREPARATION METHODS THEREFOR AND APPLICATIONS THEREOF

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Zhaopeng Hou, Beijing (CN); Xuefeng Li, Beijing (CN); Run Xu, Beijing (CN); Guofu Xia, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

(*) Notice: Subject to any disclaimer, the term of this patent is extended or adjusted under 35 U.S.C. 154(b) by 1087 days.

(21) Appl. No.: 17/755,540

(22) PCT Filed: Oct. 29, 2020

(86) PCT No.: PCT/CN2020/124784
§ 371 (c)(1),
(2) Date: Apr. 30, 2022

(87) PCT Pub. No.: WO2021/083267
PCT Pub. Date: May 6, 2021

(65) Prior Publication Data

US 2022/0387984 A1 Dec. 8, 2022

(30) Foreign Application Priority Data

Oct. 31, 2019 (CN) ......................... 201911053472.2
Oct. 31, 2019 (CN) ......................... 201911053524.6

(51) Int. Cl.
*B01J 6/00* (2006.01)
*B01J 35/51* (2024.01)
(Continued)

(52) U.S. Cl.
CPC ............ *B01J 6/001* (2013.01); *B01J 35/613* (2024.01); *B01J 35/615* (2024.01);
(Continued)

(58) Field of Classification Search
CPC ........ B01J 6/001; B01J 35/613; B01J 35/615; B01J 37/0045; B01J 37/08; B01J 35/51;
(Continued)

(56) References Cited

U.S. PATENT DOCUMENTS

| | | | | |
|---|---|---|---|---|
| 5,026,796 A * | 6/1991 | McDaniel | ............... | C08F 10/00 526/100 |
| 2014/0178262 A1* | 6/2014 | Tran | ....................... | B01J 35/647 502/340 |

FOREIGN PATENT DOCUMENTS

| | | |
|---|---|---|
| CN | 102249245 A | 11/2011 |
| CN | 103288093 A | 9/2013 |

(Continued)

OTHER PUBLICATIONS

Wang, G., Ma, J., Gao, Y. et al. "Preparation of ceria-stabilized zirconia microspheres by external gelation: size control" J Sol-Gel Sci Technol 78, 514-522 (2016) (Year: 2016).*

(Continued)

*Primary Examiner* — Daniel Berns
*Assistant Examiner* — Joshua Maxwell Speer
(74) *Attorney, Agent, or Firm* — NKL Law; Allen Xue

(57) ABSTRACT

A microsphere of oxide has an opening on its surface connected to a hollow core inside, forming a cavity. The oxide the microsphere is made of is selected from the group consisting of alumina, silica, zirconia, magnesium oxide,
(Continued)

calcium oxide and titania. The microsphere of oxide shows better mass and heat transfer characteristics, and has strength significantly higher than that of existing products with similar structures. A FT synthesis catalyst has the microsphere of oxide as a support and an active metal component disposed on the support. The active metal component is one or more selected from the group consisting of Co, Fe, and Ru.

7 Claims, 7 Drawing Sheets

(51) Int. Cl.

| | |
|---|---|
| ***B01J 35/61*** | (2024.01) |
| ***B01J 35/63*** | (2024.01) |
| ***B01J 37/00*** | (2006.01) |
| ***B01J 37/08*** | (2006.01) |
| ***C07C 1/04*** | (2006.01) |

(52) U.S. Cl.

CPC ........... *B01J 37/0045* (2013.01); *B01J 37/08* (2013.01); *C07C 1/043* (2013.01); *B01J 35/51* (2024.01); *B01J 35/612* (2024.01); *B01J 35/617* (2024.01); *B01J 35/633* (2024.01); *B01J 35/635* (2024.01); *B01J 35/638* (2024.01)

(58) Field of Classification Search

CPC ...... B01J 35/612; B01J 35/617; B01J 35/633; B01J 35/635; B01J 35/638; B01J 35/647; B01J 21/066; B01J 21/08; B01J 23/462; B01J 23/745; B01J 23/75; B01J 37/0201; B01J 37/038; B01J 37/088; B01J 21/04; C07C 1/043; C01B 33/18; C01B 33/187; C01B 33/20; C01B 33/26; C01P 2004/54; C01P 2006/12; C01P 2006/14; C01P 2006/16; C01P 2004/03; C01P 2004/34; C01P 2004/61; C01F 7/308; C01F 7/441; C01F 17/218; C01F 17/34; C01G 25/02; C01G 23/053

See application file for complete search history.

(56) References Cited

FOREIGN PATENT DOCUMENTS

| | | | | |
|---|---|---|---|---|
| CN | 104853827 A | | 8/2015 | |
| CN | 108144613 A | | 6/2018 | |
| CN | 108404970 A | | 8/2018 | |
| CN | 111185145 A | * | 5/2020 | .............. B01J 21/04 |

OTHER PUBLICATIONS

Machine Translation, P. H. Tran, CN-104853827A, Aug. 19, 2015 (Year: 2015).*

Li et al., "Facile synthesis of hierarchical porous gamma-Al2O3 hollow microspheres for water treatment", Journal of Colloid and Interface Science 417 (2014) 369-378 (Year: 2014).*

Huang et al. "Incorporation of high explosives into nano-aluminum based microspheres to improve reactivity", Chemical Engineering Journal 383 (2020) 123110 (Year: 2019).*

Machine Translation, CN-111185145-A, Chang X, May 22, 2020 (Year: 2020).*

Wang, Jinyuan et al., "Preparation of Silica-Alumina Hollow Spheres with a Single Surface Hole by Co-axial Microchannel", Chinese Journal of Chemical Engineering, vol. 22, Sep. 16, 2014, ISSN:1004-9541; pp. 1352-1356.

Ding, Shangjun et al., "New facile synthesis of TiO2 hollow sphere with an opening hole and its enhanced rate performance in lithium-ion batteries", New J. Chem., vol. 37, Jan. 7, 2013, ISSN:1144-0546; pp. 784-789.

* cited by examiner

SUPPORT AND FT SYNTHESIS CATALYST, AND PREPARATION METHODS THEREFOR AND APPLICATIONS THEREOF

TECHNICAL FIELD

The present disclosure relates to supported catalysts. In particular, the present disclosure relates to a microsphere of oxide in the shape of raspberry, an FT synthesis catalyst containing the same as a support, and their preparation methods and applications.

BACKGROUND

In the past few decades, there were a large number of documents which studied or reported hollow microspheres of inorganic materials. Compared with common solid spheres, hollow materials have a lower density and a larger specific surface area. They have been widely used, for example as supports for drugs and catalysts, as well as adsorbents for gases. In recent years, the research and application of hollow microspheres of inorganic materials are attracting more and more attention.

Hollow microspheres of alumina are a new type of high temperature resistant thermal insulation materials. They are prepared by smelting and blowing industrial alumina in an electric furnace, and have a crystalline form of $\alpha$-$Al_2O_3$. It is possible to produce articles with various shapes by using hollow microspheres of alumina as the main body. The obtained articles may have high mechanical strength, which may be several times that of common lightweight products, and may have a bulk density which is much smaller than that of solid products. They have been widely used in high temperature and ultra-high temperature furnaces such as gasification furnaces in the petrochemical industry, reaction furnaces in the carbon black industry, induction furnaces in the metallurgical industry and the like, and have achieved very satisfied effects on saving energy. At present, hollow microsphere materials of alumina may be prepared by high-temperature melting and spraying reactions, template methods, layer-by-layer (L-b-L) methods, and microemulsion methods.

Hollow microspheres of silica have been widely used in the fields such as drug supports, biosignal markers and coatings, due to their advantages such as good biocompatibility, easy availability and low cost in raw materials. The preparation of hollow microspheres of silica has attracted extensive attention from researchers. Among them, the most widely proposed is a method, comprising: using microspheres of polystyrene as a template, coating its surface with a shell of silica, and then removing the core of polystyrene to obtain hollow microspheres of silica. At present, the preparation methods reported mainly include: (1) electrostatic adsorption methods; (2) modifications with silicon-based cross-linking agents; (3) layer-by-layer methods.

Hollow microspheres of zirconia are plasma sprayed thermal insulation materials which are used for the surface modification of mechanical parts of for example aviation engines, gas turbines, and heat treatment equipments. The coating prepared from such microspheres has good thermal shock resistance and high temperature corrosion resistance. Accordingly, when sprayed on high temperature components such as aviation engines, it is possible not only to improve the mechanical performance of the engines, but also to prolong the life of the components under high temperature. Porous hollow microspheres of zirconia are chemically stable and thereby can be used as a micro support for controlled release of active substances (such as sustained release agents for drugs). They do not react with the loaded drug active ingredients, have good biocompatibility, and do not pollute the environment. In addition, they have nano-size pores and thereby make it possible to effectively control the particle size and pore size. The current methods for producing hollow microspheres of zirconia include plasma spheroidization and granulation by spray drying. The plasma spheroidization is a method which uses a plasma spray gun as a heat source to heat-treat the porous agglomerated powder of zirconia prepared by other methods to obtain the hollow microspheres.

Hollow microspheres of titania can enlarge the specific surface area of titania and thereby can provide more active sites for catalytic reactions. Additionally, their higher crystallinity can reduce the rate of recombination of photogenerated electrons with active holes, and thereby improve catalytic activity. In a further aspect, with respect to modification, the hollow structure can provide space for further modification of the titania materials. There are many methods for synthesizing hollow microspheres of titania, such as template methods, flame combustion methods, templateless methods and the like. Among them, the template method is easy to control the pore size and shell thickness of microspheres, and the dispersion is relatively uniform. However, steps of the template method are complicated, and the shell of microspheres is easily damaged during removing of the template. The flame combustion method and the templateless method have advantages, such as continuous preparation process, simple operation, and no pollution. However, the prepared products are not uniform.

Fischer-Tropsch synthesis process, also known as FT synthesis, is a process in which synthesis gas (a mixed gas of carbon monoxide and hydrogen) is used as a raw material to synthesize liquid hydrocarbons or hydrocarbons in presence of catalysts under appropriate conditions. It is a key step in the indirect conversion of non-oil resources such as coal, natural gas and biomass into high-grade liquid fuels and chemical raw materials.

In order to obtain an ideal distribution of FT synthesis products, one of the commonly used measures is to upgrade the FT synthesis catalyst, for example, by using hollow microspheres of inorganic materials as supports. However, the current methods for preparing hollow microspheres of inorganic materials generally have the problems of small scale and not easy to expand. At the same time, some preparation may have low efficiency and high cost in raw materials, which substantially limits the use of them as supports in preparing catalysts. Additionally, the prepared catalyst may not be able to meet the requirements on performances.

In fields such as petrochemical, in order to be suitable for use in fixed-bed reactors (such as microreactors, microchannel reactors, microchemical reactors, mesoscopic reactors), catalysts need to have high strength, high porosity, and low pressure drop. Therefore, there is an increasing demand for high-strength hollow microspheres of inorganic materials which may be used as supports.

It should be noted that the information disclosed in the foregoing background is only used to facilitate the understanding of the present disclosure. Accordingly, it may include information that does not constitute the prior art known to those of ordinary skill in the art.

SUMMARY OF THE DISCLOSURE

The present disclosure is to solve the problems of the prior art, by providing a microsphere of oxide in the shape of raspberry, an FT synthesis catalyst containing the same as a support, and their preparation methods and applications. The present disclosure provides microspheres of oxide with a hollow structure, which have better mass and heat transfer characteristics and significantly improved strength. The microsphere of oxide in accordance with the present disclosure is particularly suitable for use as a support for FT synthesis catalysts, and is particularly suitable for use in fixed-bed reactors, such as microreactors, microchannel reactors, microchemical reactors or mesoscopic reactors.

In order to achieve the above objectives, the present disclosure adopts the following technical solutions.

In one aspect, the present disclosure provides a microsphere of oxide in the shape of raspberry, which is a hollow microsphere with a large hole on the surface, wherein the hollow microsphere has a hollow structure inside, wherein the large hole and the hollow structure are connected to form a cavity with an open end, and wherein the oxide in the microsphere of oxide in the shape of raspberry is one or more selected from the group consisting of alumina, silica, zirconia and titania.

In some embodiments, the microsphere of oxide in the shape of raspberry has a particle size of 3-2500 μm, preferably 10-500 μm.

In some embodiments, the hollow structure has a diameter of 1-2000 μm, preferably 1-400 μm.

In some embodiments, the large hole has a diameter of 0.2-1000 μm, preferably 0.5-200 μm.

In some embodiments, the shell of the hollow microsphere has a thickness of 0.2-1000 μm, preferably 0.5-200 μm.

In some embodiments, the microsphere of oxide in the shape of raspberry has a sphericity of 0.50-0.99.

In some embodiments, microspheres of oxide in the shape of raspberry have a crushing rate of 0-1%.

In another aspect, the present disclosure provides a method for preparing the above-mentioned microsphere of oxide in the shape of raspberry, comprising the steps of:

- adding a nitrate, a peptizer, a hole-forming agent, the oxide and/or a precursor thereof to a dispersant in sequence and stirring, to obtain a dispersion slurry;
- aging the dispersion slurry; and
- sending the aged dispersion slurry into a drying device and shaping by drying under the conditions wherein the temperature of the inlet gas is 400-1200° C., preferably 450-700 C, and the temperature of the outlet gas is 50-300° C., preferably 120-200° C., to obtain the microsphere of oxide in the shape of raspberry.

In some embodiments, the nitrate is one or more selected from the group consisting of aluminum nitrate, zirconium nitrate, lanthanum nitrate and yttrium nitrate.

In some embodiments, the peptizer is one or more selected from the group consisting of acids, bases and salts.

In some embodiments, the hole-forming agent is one or more selected from the group consisting of starch, synthetic cellulose, polymeric alcohol and surfactant.

In some embodiments, the oxide and/or precursor thereof is one or more selected from the group consisting of an aluminum source, a silicon source, a zirconium source, and a titanium source, wherein the aluminum source is one or more selected from the group consisting of pseudo-boehmite, aluminum alkoxide, aluminum nitrate, aluminum sulfate, aluminum chloride and sodium metaaluminate; the silicon source is one or more selected from consisting of esters of silicate, sodium silicate, water glass and silica sol; the zirconium source is one or more selected from the group consisting of zirconium dioxide, zirconium tetrachloride, zirconyl chloride, zirconium hydroxide, zirconium sulfate, zirconium phosphate, zirconyl nitrate, zirconium nitrate, basic zirconium carbonate and zirconium tetrabutoxide; and the titanium source is one or more selected from the group consisting of titanium dioxide, metatitanic acid, titanium nitrate, titanyl sulfate, titanium dichloride, titanium trichloride, titanium tetrachloride, aluminum titanium chloride, tetraethyl titanate, tetrabutyl titanate, tetra-n-propyl titanate and tetra-isopropyl titanate.

In some embodiments, the dispersant is one or more selected from the group consisting of water, alcohols, ketones, and acids.

In some embodiments, the mass ratio of the nitrate, the peptizer, the hole-forming agent, and the oxide and/or precursor thereof is (10-500):(1-10):(10-500):(10-1000).

In some embodiments, a blasting agent may be added to the dispersant, wherein the blasting agent is one or more selected from the group consisting of picric acid, trinitrotoluene, mercury fulminate, nitroglycerin, nitrocellulose, Dana explosive, hexogen, lead azide and C4 plastic explosive.

In some embodiments, the blasting agent is added in an amount of 0-1% of the total dry weight of the nitrate, the peptizer, the hole-forming agent, and the oxide and/or precursor thereof.

In some embodiments, the drying device is a flash drying device or a spray drying device.

In some embodiments, the aging is operated at a temperature of 0-90° C., preferably 20-60° C.

In a further aspect, the present disclosure provides a FT synthesis catalyst comprising a support and an active metal component supported on the support, wherein the active metal component is one or more selected from the group consisting of Co, Fe and Ru, the support is a microsphere of oxide in the shape of raspberry, which is a hollow microsphere with a large hole on the surface, wherein the hollow microsphere has a hollow structure inside, wherein the large hole and the hollow structure are connected to form a cavity with an open end, and wherein the oxide in the microsphere of oxide in the shape of raspberry is one or more selected from the group consisting of alumina and silica.

In some embodiments, based on the weight of the catalyst, the support is present in the catalyst in an amount of 25-95 wt %, preferably 30-90 wt %, on oxide basis, and the active metal component is present in the catalyst in an amount of 5-75 wt %, preferably 10-70 wt %, on oxide basis.

In some embodiments, the microsphere of oxide in the shape of raspberry has a particle size of 3-2500 μm, preferably 10-500 μm, and a sphericity of 0.50-0.99.

In some embodiments, the hollow structure has a diameter of 1-2000 μm, preferably 1-400 μm.

In some embodiments, the large hole has a diameter of 0.2-1000 μm, preferably 0.5-200 μm.

In some embodiments, the shell of the hollow microspheres has a thickness of 0.2-1000 μm, preferably 0.5-200 μm.

In some embodiments, microspheres of oxide in the shape of raspberry have a crushing rate of 0-1%.

In a further aspect, the present disclosure provides a method for preparing the above-mentioned FT synthesis catalyst, comprising the steps of:

- providing the microsphere of oxide in the shape of raspberry and an impregnating solution of a compound containing the active metal component;
- calcining the microsphere of oxide in the shape of raspberry, to obtain the support; and impregnating the support with the impregnation solution, subjecting to drying and activation by calcining, to obtain the FT synthesis catalyst.

In some embodiments, the step of providing the microsphere of oxide in the shape of raspberry may include:

adding a nitrate, a peptizer, a hole-forming agent, an aluminum source and/or an silicon source to a dispersant and stirring, to obtain a dispersion slurry;

aging the dispersion slurry; and sending the aged dispersion slurry into a drying device and shaping by drying under the conditions wherein the temperature of the inlet gas is 400-1200° C., preferably 450-700° C., and the temperature of the outlet gas is 50-300° C., preferably 120-200° C., to obtain the microsphere of oxide in the shape of raspberry.

In some embodiments, the nitrate is one or more selected from the group consisting of aluminum nitrate, zirconium nitrate, lanthanum nitrate, and yttrium nitrate.

In some embodiments, the peptizer is one or more selected from the group consisting of acids, bases and salts.

In some embodiments, the hole-forming agent is one or more selected from the group consisting of starch, synthetic cellulose, polymeric alcohol and surfactant.

In some embodiments, the aluminum source is one or more selected from the group consisting of pseudo-boehmite, aluminum alkoxide, aluminum nitrate, aluminum sulfate, aluminum chloride, and sodium metaaluminate, and the silicon source is one or more selected from the group consisting of silicate esters, sodium silicate, water glass and silica sol.

In some embodiments, the dispersant is one or more selected from the group consisting of water, alcohols, ketones, and acids.

In some embodiments, the mass ratio of the nitrate, the peptizer, the hole-forming agent, and the oxide and/or precursor thereof is (10-500):(1-10):(10-500):(10-1000).

In some embodiments, a blasting agent may be added to the dispersant, wherein the blasting agent is one or more selected from the group consisting of picric acid, trinitrotoluene, nitroglycerin, nitrocellulose, Dana explosive, hexogen and C4 plastic explosive, and the blasting agent is added in an amount of 0-1% of the total dry weight of the nitrate, the peptizer, the hole-forming agent, and the aluminum source and/or the silicon source.

In some embodiments, the drying device is a flash drying device or a spray drying device.

In some embodiments, the aging is operated at a temperature of 0-90° C., preferably 20-60° C.

In some embodiments, the calcining is operated at a temperature of 400-1300° C., preferably 450-1100° C., more preferably 500-700° C., the drying is operated at a temperature is 80-200° C., preferably 100-150° C., and the activation by calcining is operated at a temperature of 200-800° C., preferably 300-600° C.

In a further aspect, the present disclosure provides the use of the above-mentioned FT synthesis catalyst in Fischer-Tropsch synthesis.

The method for preparing microspheres of oxide in the shape of raspberry with the cavity structure in accordance with the present disclosure has strong controllability, low cost and high efficiency, and is suitable for large-scale industrial applications.

The microspheres of oxide in the shape of raspberry in accordance with the present disclosure can be applied in various fields, such as heat-resistant materials, biomaterials, photochemical materials and the like, and all exhibit special advantages. Especially in the field of catalysts, it shows better mass and heat transfer characteristics, and has strength which is significantly higher than that of existing products with similar structures. When used in fixed-bed reactors (such as micro-reactors, micro-channel reactors, micro-chemical reactors or mesoscopic reactors), it shows large porosity and small pressure drop, and thereby can be widely used in petrochemical and other fields.

The cavity structure imparts the FT synthesis catalyst in accordance with the present disclosure with short diffusion distance and large surface area. It solves the diffusion problem in FT synthesis reaction, can improve the conversion of FT synthesis and the selectivity to C5+ hydrocarbons, and reduce the selectivity to methane and $CO_2$. In addition, the selectivity to methane will not increase significantly due to the increase in temperature.

DETAILED DESCRIPTION

Figure 1:
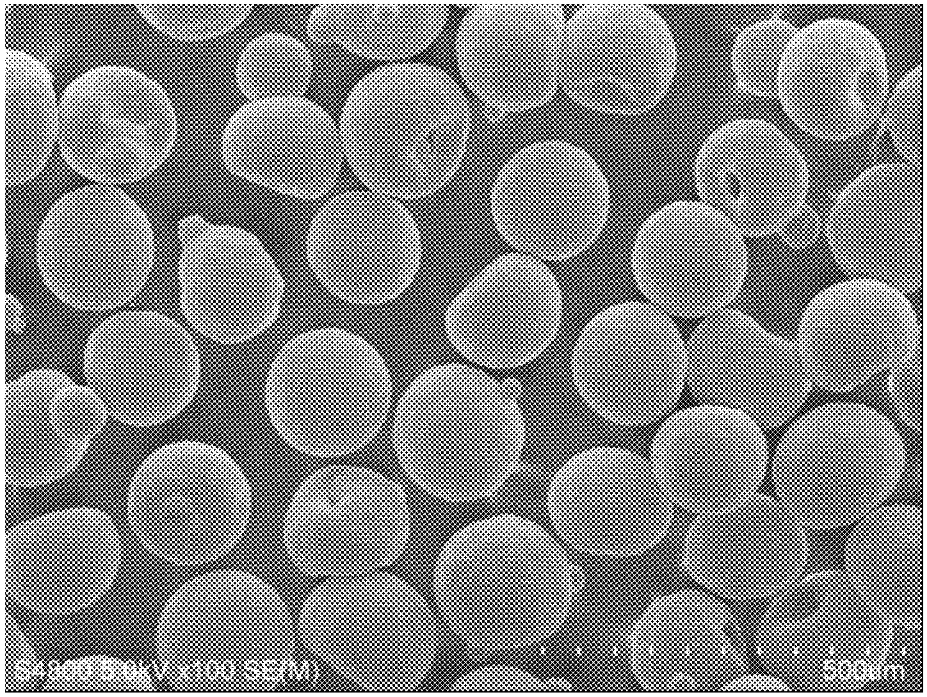
FIG. 1 to 4 are SEM photos of the microsphere of oxide in the shape of raspberry prepared in the Preparation Examples 1-4.

The present application will be further described in detail below with reference to embodiments thereof. It is to be understood that the embodiments described herein are merely illustrative and not restrictive.

In the present disclosure, except for those explicitly stated, any matter or matters not mentioned are directly applicable to those known in the art without any change. Moreover, any one of the embodiments described herein can be freely combined with one or more of other embodiments described herein, and the resulting technical solution or technical idea should be considered as a part of the original disclosure or original description of the present disclosure, while should not be considered as a new matter that has not been disclosed or anticipated herein, unless it is apparent to those skilled in the art that such a combination is obviously unreasonable.

All the features disclosed in the present disclosure can be freely combined, and those combinations should be understood as the content disclosed or recorded in the present disclosure, unless it is apparent to those skilled in the art that such combinations are obviously unreasonable. It should be understood that the endpoints and any value in the ranges disclosed herein are not limited to the precise range or value, but encompass values close to those ranges or values. For ranges of values, it is possible to combine between the endpoints of each of the ranges, between the endpoints of each of the ranges and the individual points, and between the individual points to give one or more new ranges of values as if these ranges of values are specifically disclosed herein. Other than in the examples, all numerical values of parameters in this specification are to be understood as being modified in all instances by the term "about" whether or not "about" actually appears before the numerical values.

According to one aspect of the present disclosure, the present disclosure provides a microsphere of oxide in the shape of raspberry, which is a hollow microsphere with a raspberry like structure, wherein the hollow microsphere has a large hole on the surface and a hollow structure inside, wherein the large hole and the hollow structure are connected to form a cavity with an open end, and wherein a powder of the microsphere of oxide in the shape of raspberry has a crushing rate of 0-1%.

The oxide in the microsphere of oxide in the shape of raspberry may be an inorganic oxide, which may be one or more selected from the group consisting of alumina, silica, zirconia, magnesium oxide, calcium oxide and titania, preferably one or more selected from the group consisting of alumina, silica, zirconia and titania.

The microsphere of oxide in the shape of raspberry has a particle size of 3-2500 μm, preferably 10-500 μm, wherein the hollow structure has a diameter of 1-2000 μm, preferably 1-400 μm, and the large hole on the surface has a diameter of 0.2-1000 μm, preferably 0.5-200 μm. The microsphere of oxide in the shape of raspberry has a shell layer surrounding the cavity, wherein the thickness thereof is 0.2-1000 μm, preferably 0.5-200 μm.

The microsphere of oxide in the shape of raspberry has a sphere like appearance, where the sphericity thereof is 0.50-0.99.

The sphericity of the microspheres may be calculated according to the following formula:

$$\sigma=4\pi A/L^2$$

where: σ is the sphericity; A is the projected area of the microsphere, in $m^2$; L is the projected perimeter of the microsphere, in m; A and L are obtained by treating the SEM photos of the microsphere with the image processing software Image-Pro Plus.

The crushing rate of powder of the microsphere of oxide in the shape of raspberry in accordance with the present disclosure is measured according to the method provided in the standard Q/SH3360 226-2010 for similar strength. In particular, the method comprises:

- selecting sieves S1 and S2 with mesh sizes of M1 and M2 respectively, where M1<M2, sieving the microsphere powder to be tested via the sieve S1 with mesh size of M1, further sieving the microsphere powder passed through the sieve S1 via the sieve S2 with mesh size of M2, and using the microsphere powder cut off by the sieve S2 as the sample to be tested;
- adding a certain amount of the sample to be tested into a steel cylinder container with a cross-sectional diameter of 10 mm, pressing via a cylinder to apply a certain pressure to the microsphere powder as the sample to be tested for a certain period of time, and sieving the pressed microsphere powder via the sieve S2 with mesh size of M2, recording the mass of the microsphere powder passed through the sieve S2, and calculating the crushing rate of the microsphere powder by dividing the mass of the microsphere powder passed through the sieve S2 by the total mass of the microsphere powder added.

In the present disclosure, M1 may be 100 meshes, M2 may be 150 meshes, the pressure may be 100N, and the time may be 10 s.

The crushing rate may be used to evaluate the strength of the microspheres. The lower crushing rate indicates the higher strength of the microspheres.

The powder of the microsphere of oxide in the shape of raspberry in accordance with the present disclosure achieves a low crushing rate under the above conditions, which indicates that it has a strength significantly higher than those of the currently known microspheres of oxide, such as the hollow microspheres of molecular sieve in the shape of apple disclosed in CN108404970A. It is attributable to the difference in raw materials and preparation methods used. The microspheres of oxide in the shape of raspberry in accordance with the present disclosure have larger porosity and higher strength. When used in a fixed-bed reactor, they may greatly reduce the pressure drop, and have excellent processability and wear resistance performance. The catalyst prepared by using them as a support may have a short reaction diffusion distance and thereby may have a promising application. They may also be made into high temperature resistant thermal insulation materials, biological materials and photochemical materials.

According to a further aspect of the present disclosure, the present disclosure provides a FT synthesis catalyst comprising a support and an active metal component supported on the support. The active metal component is a group VIII metal component, preferably one or more selected from the group consisting of Co, Fe and Ru. The active metal components may have activity in the order of Ru>Co>Fe, and possibility for chain growth roughly in the order of Ru>Co≈Fe. The support may be the microsphere of oxide in the shape of raspberry mentioned above, wherein the oxide in the microsphere of oxide in the shape of raspberry is one or more selected from the group consisting of alumina and silica.

In the FT synthesis catalyst in accordance with the present disclosure, based on the weight of the catalyst, the support is present in an amount of 25-95 wt %, preferably 30-90 wt %, on oxide basis, and the active metal component is present in an amount of 5-75 wt %, preferably 10-70 wt %, more preferably 12-30 wt %, on oxide basis.

The FT synthesis catalyst in accordance with the present disclosure may be used in a fixed-bed reactor, such as a microchannel reactor, for Fischer-Tropsch synthesis reaction.

The microsphere of oxide in the shape of raspberry in accordance with the present disclosure may be prepared by a method which may include:

- adding a nitrate, a peptizer, a hole-forming agent and the oxide or a precursor thereof to a dispersant and stirring, to obtain a dispersion slurry;
- aging the dispersion slurry; and
- sending the aged dispersion slurry into a drying device and shaping by drying under the conditions wherein the temperature of the inlet gas is 400-1200° C., preferably 450-700° C., and the temperature of the outlet gas is 50-300° C., preferably 120-200° C., to obtain the microsphere of oxide in the shape of raspberry.

In the above method in accordance with the present disclosure, the nitrate is one or more selected from the group consisting of aluminum nitrate, zirconium nitrate, lanthanum nitrate and yttrium nitrate. Nitrate ions in nitrates may be used as oxidants for the hole-forming agent under high temperature conditions. They undergo self-propagating combustion reactions at high temperatures, explosively generating gas and steam so that cavities form in the oxide materials.

In the above method in accordance with the present disclosure, the peptizer is one or more selected from the group consisting of acids, bases and salts. The acids may be selected from the group consisting of inorganic acids (such as hydrochloric acid, sulfuric acid, nitric acid, and the like), organic acids (formic acid, acetic acid, oxalic acid, and the like) and combinations of one or more of inorganic acids or organic acids. The bases may be selected from the group consisting of inorganic bases (sodium hydroxide, potassium hydroxide, barium hydroxide, calcium hydroxide, aluminum hydroxide, lithium hydroxide, magnesium hydroxide, zinc hydroxide, copper hydroxide, ferric hydroxide, lead hydroxide, cobalt hydroxide, chromium hydroxide, zirconium hydroxide, nickel hydroxide, ammonium hydroxide, soda ash (anhydrous sodium carbonate), sodium carbonate (monohydrate, heptahydrate, and decahydrate thereof), sodium bicarbonate (baking soda), potassium carbonate, potassium bicarbonate, and the like), organic bases (such as amine compounds, alkali metal salts of alcohols, alkaloids, alkyl metal lithium compounds, and the like) and combinations of one or more of inorganic bases or organic bases. The salts may be selected from the group consisting of salts of inorganic acids (such as hydrochloride, sulfate, nitrate, and the like), salts of organic acids (format, acetate, oxalate, and the like), and combinations of one or more salts of inorganic acids or salts of organic acids.

In the above method in accordance with the present disclosure, the hole-forming agent is one or more selected from the group consisting of starch, synthetic cellulose, polymeric alcohol and surfactant. The synthetic cellulose is preferably one or more of carboxymethyl cellulose, methyl cellulose, ethyl cellulose, and hydroxycellulose fatty alcohol polyvinyl ether. The polymeric alcohol is preferably one or more of polyethylene glycol, polypropanol, polyvinyl alcohol and polypropylene alcohol (PPG). The surfactant is preferably one or more of fatty alcohol polyvinyl ether, fatty alcohol amide and its derivatives, acrylic acid copolymers and maleic acid copolymers with molecular weight of 200-2000000.

In the method in accordance with the present disclosure, the oxide and/or precursor thereof may directly be alumina, silica, zirconia and titania, or may be precursors for forming those oxides. In particular, they may be one or more selected from the group consisting of aluminum sources, silicon sources, zirconium sources and titanium sources. The aluminum source is one or more selected from the group consisting of pseudo-boehmite, aluminum alkoxide, aluminum nitrate, aluminum sulfate, aluminum chloride and sodium metaaluminate. The silicon source is one or more selected from the group consisting of silicate esters, sodium silicate, water glass and silica sol. The zirconium source is one or more selected from the group consisting of zirconium dioxide, zirconium tetrachloride, zirconyl chloride, zirconium hydroxide, zirconium sulfate, zirconium phosphate, zirconyl nitrate, zirconium nitrate, basic zirconium carbonate and zirconium tetrabutoxide. The titanium source is one or more selected from the group consisting of titanium dioxide, metatitanic acid, titanium nitrate, titanyl sulfate, titanium dichloride, titanium trichloride, titanium tetrachloride, aluminum titanium chloride, tetraethyl titanate, tetrabutyl titanate, tetra-n-propyl titanate, and tetraisopropyl titanate.

When using the above aluminum source, silicon source, zirconium source and titanium source, chemical reagents that precipitate or gelate them may be further comprised, such as acids (for example inorganic acids such as hydrochloric acid, sulfuric acid, nitric acid, or organic acids such as acetic acid), and/or bases (such as sodium carbonate, sodium hydroxide, and the like).

When it is necessary to prepare an oxide composition containing other ingredients, oxides such as vanadium oxide, chromium oxide, manganese oxide, molybdenum oxide, tungsten oxide, iron oxide, cobalt oxide, nickel oxide, copper oxide and the like may be further comprised. The precursors of those oxides may be used.

The precursors of the oxides may be converted into the corresponding oxides under the conditions of the method in accordance with the present disclosure.

In the method in accordance with the present disclosure, the dispersant is one or more selected from the group consisting of water, alcohols, ketones and acids. The alcohols may be methanol, ethanol, propanol, and the like. The ketones may be acetone, butanone, and the like. The acids may be formic acid, acetic acid, propionic acid, and the like. Preferably, the dispersant is a mixture of water and a small amount of ethanol. The small amount of ethanol may have a better dispersion effect in water and can be used as a boiling point regulator to adjust the dispersant so that the effect of evaporating water and the effect of shrinking the droplet are more matched, so as to make the appearance of the microspheres more uniform and smooth.

In the method in accordance with the present disclosure, the mass ratio of the nitrate, the peptizer, the hole-forming agent and the oxide and/or precursor thereof is (10-500):(1-10):(10-500):(10-1000).

In the method in accordance with the present disclosure, the nitrate, the peptizer, the hole-forming agent, and the oxide and/or precursor thereof may be added to the dispersant in sequence, or added at the same time. The order of adding can also be adjusted based on the dissolution of each raw material. While they are added, they may be stirred to make them evenly mixed.

The method in accordance with the present disclosure may further comprise adding a blasting agent to the dispersant, before or after the adding of the oxides. The blasting agent is one or more selected from the group consisting of picric acid, trinitrotoluene, nitroglycerin, nitrocellulose, Dana explosive, hexogen and C4 plastic explosive. Before the shaping by drying, the blasting agent should be mixed evenly with other materials. The blasting agent is present in an amount of 0-1% of the total dry weight of the nitrate, the peptizer, the hole-forming agent and the oxide and/or precursor thereof.

In the method in accordance with the present disclosure, the nitrate, the peptizer, the hole-forming agent and the oxide or precursor thereof are sequentially added to the dispersant to make a slurry. The slurry is stirred evenly and then pumped into a sand mill or colloid mill for grinding, to obtain the dispersion slurry. During the making of the slurry, the slurry generally has a solid content of 5-60 wt %. The time for the grinding is 1-30 minutes. After the mixing and grinding, the average particle size of particles of the aluminum source, silicon source, zirconium source and titanium source in the slurry may be ground to 0.01-10 μm.

After the mixing and grinding, raw materials are fully dissolved and dispersed to make the dispersion slurry uniform. The grinding equipment used may be a colloid mill, a sand mill or other equipments. The selection criterion is that the powder of catalyst is ground to the required average particle size, i.e. less than 10 μm.

Afterwards, the dispersion slurry is subjected to aging at a temperature of 0-90° C. for time of 0.1-24 hours, preferably 0.5-2 hours.

After the aging, the dispersion slurry is sent into a drying device and subjected to shaping by drying under the conditions wherein the temperature of the inlet gas is 400-1200° C., preferably 450-700° C., and the temperature of the outlet gas is 50-300° C., preferably 120-200° C., and a conventional pressure, to obtain the microsphere of oxide in the shape of raspberry.

The drying device used in the present disclosure may be a flash drying device and a spray drying device, preferably a spray drying device. Flash drying and spray drying are common methods used for drying materials. After the wet material is dispersed in the drying tower, by contacting with the hot air, the moisture is quickly vaporized to obtain a dry product. The spray drying method can directly dry a solution and an emulsion into powdery or granular products, eliminating the need for procedures such as evaporation, pulverization and the like.

The working principle of spray drying is to disperse the material to be dried into very fine, mist-like particles through mechanical actions (such as pressure, centrifugal force, airflow spray), which increases the evaporation area of water and accelerates the drying process. By contacting with hot air, most of water is removed in a short time, so that the solid matter in the material is dried into powders.

The spray drying device used in the present disclosure may be a conventional device in the existing process. There is not special limitation on the same in the present disclosure. In general, a spray drying device may include a feeding system, a hot gas system, a drying tower system, a receiving system and a sealing system. The feeding system is connected with the drying tower system at the middle of the top end, the hot gas system is connected with the drying tower system at the side of the top end, the receiving system is connected with the drying tower system at the bottom end, and the sealing system is connected with the hot gas system. In general, a spray drying process may necessarily involve three functions: the spraying of the original liquid; the drying of the tiny droplets in the spray; and the separation and recovery of fine powder products. The spray drying device is usually equipped with an atomizer, a drying chamber, and a fine powder recovery device corresponding to the above-mentioned functions.

The spray drying process may involve many control parameters and complex factors. Accordingly, the products after the spray drying may have very complicated particle sizes and particle shapes. Generally, the product may have a particle size in the range of micron order, and may be a mixture of different shapes including spherical, disc, apple, grape, cavity, meniscus, and the like. Among others, it is hard to selectively shape the product into an ideal single shape, such as cavity.

One method in the prior art involves forming a molecular sieve-containing dispersion into a spherical emulsion by means of the surface tension of a surfactant, and then subjecting the spherical emulsion to shaping by spraying at a lower temperature. During the shaping by spraying, the hole-forming agent in the spherical emulsion may be vaporized or pyrolyzed. The gas generated by vaporization and pyrolysis may make the internal part of the spherical emulsion hollow. The slow release of the gas causes the formation of large holes on the surface, and the large holes are connected to the internal hollow structure. In addition, during the shaping by spraying, the molecular sieve particles may form secondary accumulation pores which become mesopores on the surface of microspheres of the molecular sieve. In combination with the subsequent calcining, hollow microspheres of molecular sieve are obtained as large particles.

In the present disclosure, the shaping by drying is performed at a high temperature, with a temperature of the inlet gas of 400-1200° C. In this process, the nitrate and the hole-forming agent inside the droplet undergo a strong oxidation-reduction reaction, resulting in self-propagating combustion and a strong explosion. Accordingly, a large amount of gas is generated instantaneously. At the same time, when the droplet is sprayed into the high-temperature zone, strong evaporation occurs at the surface. The resulting surface tension may cause the droplets to shrink sharply. The combined effect of the strong internal explosion and the strong external shrinkage forms a hollow material in the shape of raspberry with very high strength. Therefore, the prepared microspheres of oxide in the shape of raspberry may have high strength, high sphericity and high rate of qualified products.

According to a further aspect of the present disclosure, the present disclosure provides a microsphere of oxide in the shape of raspberry prepared by the method in accordance with the present disclosure as described above.

The microsphere of oxide in the shape of raspberry in accordance with the present disclosure may be used as a support after being calcined. By loading corresponding active components, it may be prepared into a variety of catalysts. The calcining may be operated at a temperature of 400-1300° C., preferably 450-1100° C., and more preferably 500-700° C., for a time of 1-12 h, preferably 2-8 h, and more preferably 3-4 h.

The support prepared from the microsphere of oxide in the shape of raspberry in accordance with the present disclosure may have a specific surface area of about 0.1-900 $m^2/g$, and preferably 10-300 $m^2/g$, and a pore volume of about 0.01-3.6 mL/g, and preferably 0.1-0.9 mL/g.

In addition, the microsphere of oxide in the shape of raspberry in accordance with the present disclosure may also be used as high temperature resistant thermal insulation materials, biological materials, pharmaceutical materials or photochemical materials, such as photocatalytic materials.

The FT synthesis catalyst in accordance with the present disclosure may be prepared by a method which may include:

- providing a microsphere of oxide in the shape of raspberry;
- calcining the microsphere of oxide in the shape of raspberry, to obtain the support; and
- impregnating the support with an impregnation solution of a compound containing the active metal component, subjecting to drying and activation by calcining, to obtain the FT synthesis catalyst.

In the method in accordance with the present disclosure, the providing of the microsphere of oxide in the shape of raspberry may include preparing the microsphere of oxide in the shape of raspberry by the method described above.

In the impregnation solution of the compound containing the active metal component, the compound containing the active metal component is one or more selected from the group consisting of their soluble compounds, such as one or more of nitrates, acetates, basic carbonates, hydrochlorides and soluble complexes containing the active metal component, preferably nitrates and/or basic carbonates. Taking cobalt as an example, the compound containing the active metal component is one or more selected from the group consisting of cobalt nitrate, cobalt acetate, cobalt bicarbonate, cobalt chloride and a soluble complex of cobalt, preferably cobalt nitrate and/or cobalt bicarbonate.

The impregnating the support with the impregnation solution of the compound containing the active metal component may include: preparing the impregnation solution of the compound containing the active metal component, and then impregnating the support with the solution. The impregnating may be performed by a conventional method, for example, excess liquid impregnation, pore saturation impregnation method, and the like. By adjusting and controlling the concentration and amount of the impregnating solution of the compound containing the active metal component, or the amount of the support, a catalyst with a specified content of the active metal component can be prepared, which is easily understood and achieved by those skilled in the art.

After impregnation, the impregnated product needs to be dried. The drying may be operated at a temperature of 80-200° C., preferably 100-150° C. The used drying device and the operation conditions are those commonly used in the existing drying technology. There is not specific limitation on them in the present disclosure.

The dried product needs to be activated by calcining, to obtain the catalyst. The activation by calcining may be operated at a temperature of 200-800° C., preferably 300-600° C. The used equipment and the operation conditions are those commonly used in the prior art related to calcining. There is not specific limitation on them in the present disclosure.

The use of the microsphere of oxide in the shape of raspberry may reduce the waste of supports and catalysts, and thereby save materials. At the same time, the shape efficiency factor may be improved due to the hollow structure, which may promote diffusion, and improve reaction efficiency and selectivity to the target product. In reactions with relatively large thermal effects, the hollow support can also reduce the generation of hot spots, and thereby has good intrinsic safety.

The use of the microsphere of oxide in the shape of raspberry as a support may result in a short diffusion distance and a large surface area. Accordingly, it solves the diffusion problem in FT synthesis reaction. The FT synthesis catalyst in accordance with the present disclosure has good FT synthesis performance. It can improve the conversion of FT synthesis and the selectivity to C5+ hydrocarbons, and reduce the selectivity to methane and $CO_2$. In addition, the selectivity to methane will not increase significantly due to the increase in temperature. Additionally, the method in accordance with the present disclosure has low cost and can be applied in large-scale industrial applications.

The following describes the present disclosure in detail with reference to the examples. However, the scope of the present disclosure is not limited thereby.

EXAMPLES

Reagents, Instruments and Tests

The specifications of some raw materials used in the following preparation examples and working examples were listed as follows:

pseudo-boehmite powder (produced by Changling Catalyst Factory, with a solid content of 69.5 wt % and a content of $\gamma$-$Al_2O_3$ not less than 98 wt %);

aluminum sol (produced by Zhoucun Catalyst Factory, with a $Al_2O_3$ content of 22 wt %);

sodium silicate (from Jinan Huifengda Chemical Co., Ltd., with a modulus of 3.1-3.4 and a content of insoluble species of less than 0.4%)

aqua ammonia, hydrochloric acid, nitric acid, sulfuric acid, aluminum sulfate, aluminum chloride, zirconium hydroxide, zirconyl chloride, titanium tetrachloride, titanium dioxide (from China National Pharmaceutical Group Chemical Reagent Co., Ltd., industrial grade);

polyethylene glycol PEG4000 powder (from Wenzhou Shuangxiao Rubber and Plastic Material Co., Ltd.);

methyl cellulose (Hubei Jiangmin Taihua Chemical Co., Ltd.);

ethyl orthosilicate (TEOS, from Jinan Huate Chemical Co., Ltd., with a content of about 99%);

aluminum nitrate, titanium nitrate, zirconium nitrate, yttrium nitrate, magnesium nitrate (from Yutai Qixin Chemical Co., Ltd., industrial grade)

Testing Methods:

1. The crushing rate of powders of the supports and the catalysts was measured according to the following method:

The microsphere powder to be tested was sieved via a 100-mesh sieve. The microsphere powder passed through the sieve was further sieved via a 150-mesh sieve. The microsphere powder cut off by the 150-mesh sieve was used as the sample to be tested. A certain amount of the microsphere powder (with a particle size of 100-150 mesh) was added into a steel cylinder container with a cross-sectional diameter of 10 mm. The microsphere powder was pressed via a cylinder to apply a certain pressure (100N) for a certain period of time (10 s). The pressed microsphere powder was sieved via the 150-mesh sieve. The mass of the microsphere powder passed through the sieve was recorded. The crushing rate of the microsphere powder was obtained by dividing the mass of the microsphere powder passed through the sieve by the total mass of the microsphere powder added.

2. The pressure drop of the catalyst bed was measured with:

a precision standard pressure gauge connected to the inlet end of the bed, wherein the gas space velocity was 24000 $h^{-1}$, and the gas medium was nitrogen.

3. The FT synthesis reaction performance of the catalyst was evaluated in a fixed bed reactor.

Before the FT synthesis catalyst was used, the catalyst was reduced to elemental metals. The conditions for reducing the catalyst included: a normal pressure, a heating rate of 5° C./min, a hydrogen space velocity of 600 $h^{-1}$, a temperature of 400° C., and for a time of 5 hours. After the reduction, the reaction performance was tested under the following conditions: raw gas composition of $H_2/CO/N_2$=45%/45%/10% (by volume), a pressure of 2.5 MPa, a temperature of 200° C., 210° C. and 220° C. respectively, and a space velocity of synthesis gas (raw gas) of 24000 $h^{-1}$. The reaction was operated at each reaction temperature for 12 hours, then a gas sample was taken for chromatographic analysis.

Preparation Example 1

20 kg of water was added into a reaction autoclave. To it, 1.2 kg of aluminum nitrate was added, then 200 g of concentrated nitric acid, and then 2.3 kg of PEG4000, and finally 4 kg of pseudo-boehmite powder. The mixture was stirred evenly and ground to obtain a dispersion slurry.

The dispersion slurry was stirred and aged at 35° C. for 1.5 hours.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas at the beginning of drying was 580° C., and the temperature of the outlet gas at the end of drying was 160° C.

Figure 5:
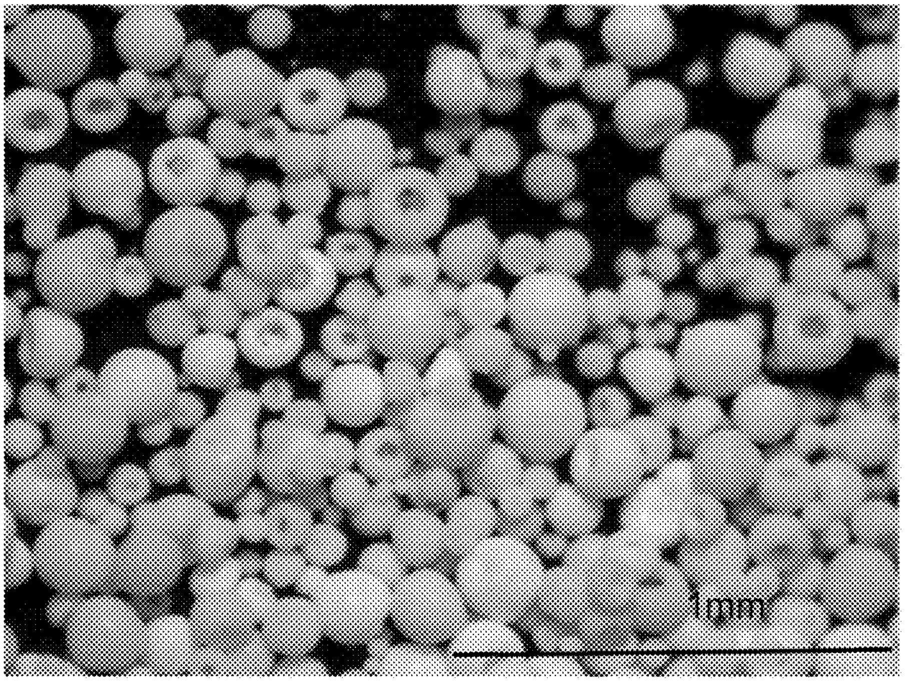
FIG. 5 is a microscopic photo of the microsphere of oxide in the shape of raspberry prepared in the Preparation Example 1.

The SEM photo of the microspheres of oxide in the shape of raspberry was shown in FIG. 1, and the microscopic photo thereof was shown in FIG. 5.

Preparation Example 2

20 kg of water was added into a reaction autoclave. To it, 0.5 kg of zircon nitrate was added, then 175 g of concentrated nitric acid, and then 2 kg of PEG4000 and 5 g nitroglycerin, and finally 4.6 kg of pseudo-boehmite powder. The mixture was stirred evenly and ground to obtain a dispersion slurry.

The dispersion slurry was stirred and aged at 25° C. for 0.5 hours.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas at the beginning of drying was 560° C., and the temperature of the outlet gas at the end of drying was 140° C.

Figure 2:
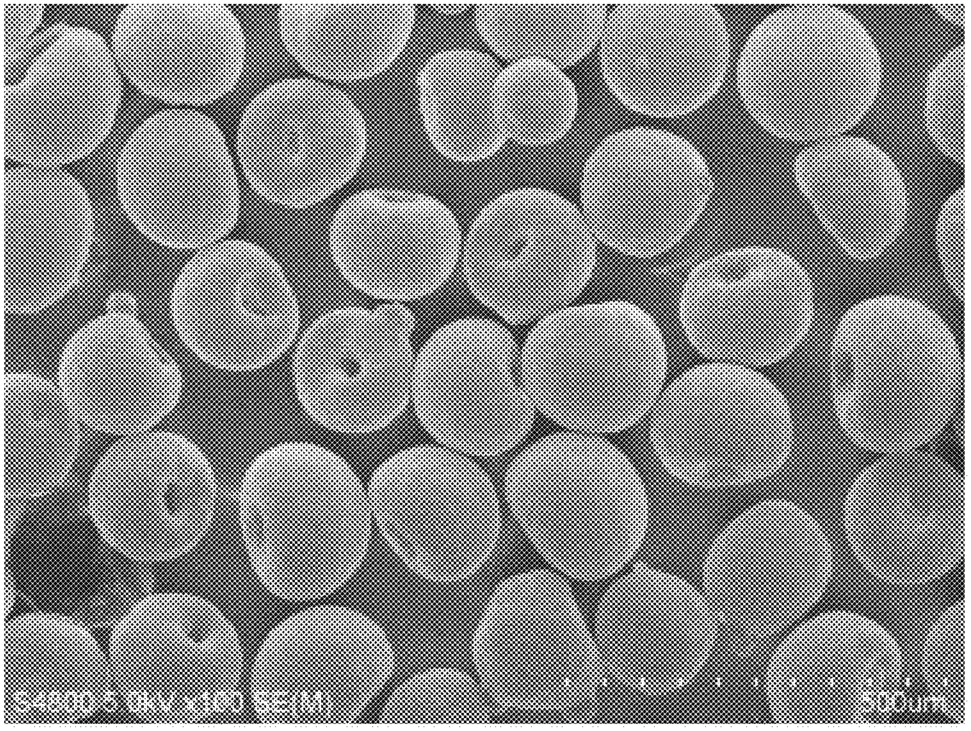

The SEM photo of the microspheres of oxide in the shape of raspberry was shown in FIG. 2.

Preparation Example 3

30 kg of water was added into a reaction autoclave. To it, 1.2 kg of aluminum nitrate was added, then 200 g of concentrated nitric acid and 4.5 kg sodium carbonate, and then 2.3 kg of methyl cellulose and 10 g picric acid, and finally 14 kg of aluminum sulfate. The mixture was stirred evenly and ground to obtain a dispersion slurry.

The dispersion slurry was stirred and aged at 30° C. for 1 hour.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas at the beginning of drying was 580° C., and the temperature of the outlet gas at the end of drying was 130° C.

Figure 3:
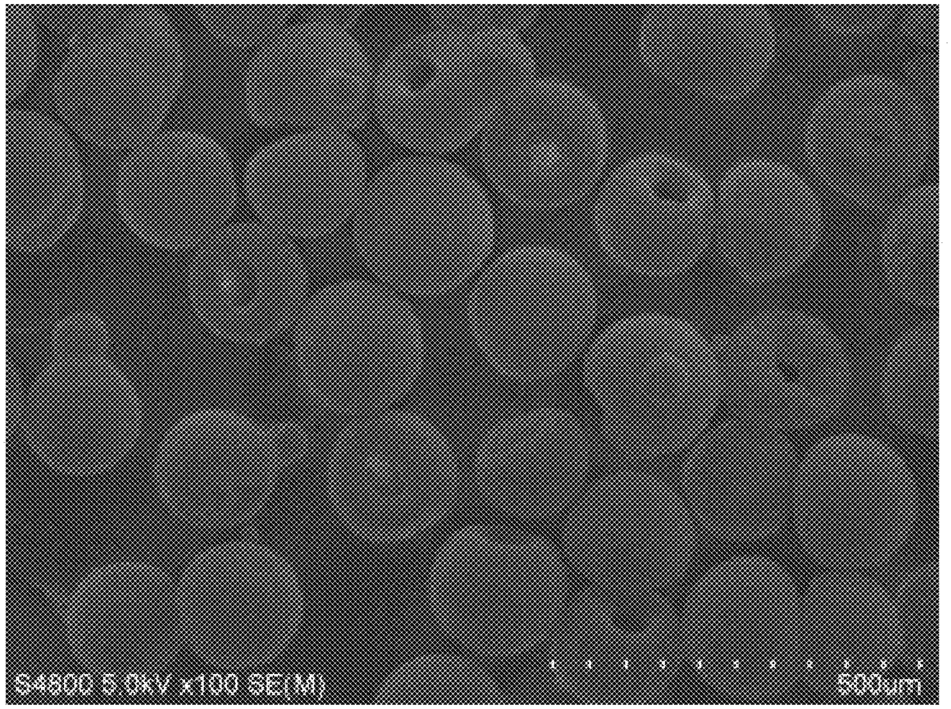

The SEM photo of the microspheres of oxide in the shape of raspberry was shown in FIG. 3.

Preparation Example 4

40 kg of water was added into a reaction autoclave. To it, 1.2 kg of yttrium nitrate was added, then 230 g of concentrated nitric acid and 4.8 kg sodium carbonate, and then 2.8 kg of methyl cellulose and 15 g nitrocellulose, and finally 12.5 kg of aluminum chloride. The mixture was stirred evenly and ground to obtain a dispersion slurry.

The dispersion slurry was stirred and aged at 30° C. for 1.5 hours.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas at the beginning of drying was 560° C., and the temperature of the outlet gas at the end of drying was 141° C.

Figure 4:
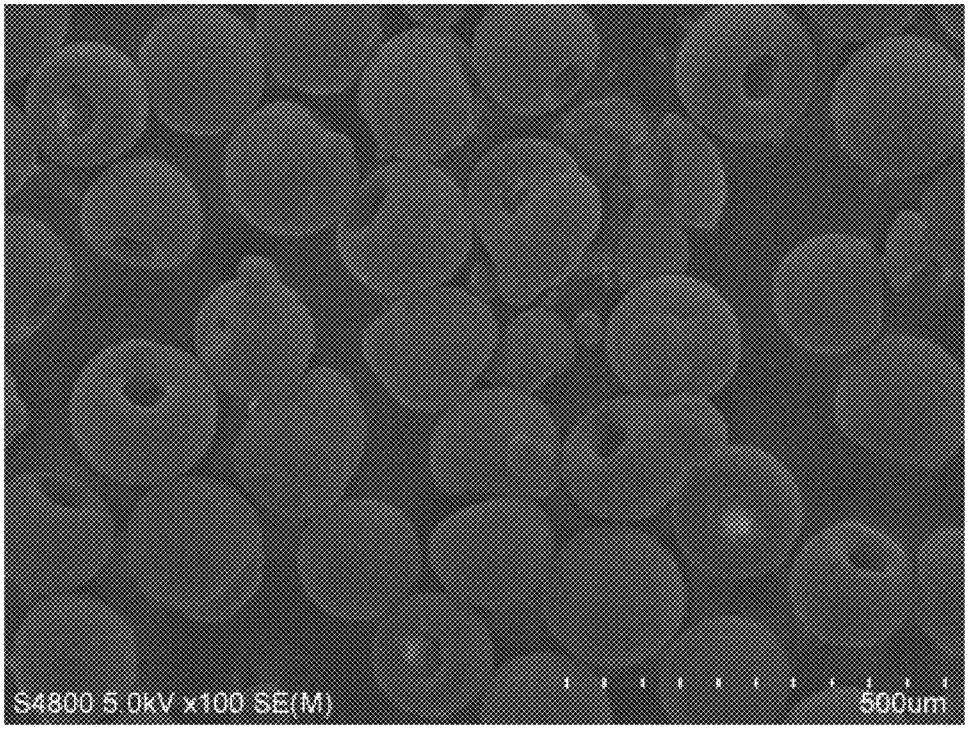

The SEM photo of the microspheres of oxide in the shape of raspberry was shown in FIG. 4.

Preparation Example 5

40 kg of water was added into a reaction autoclave. To it, 1.2 kg of aluminum nitrate was added, then 200 g of concentrated nitric acid, and then 2 kg of PEG4000 and 2 g nitrocellulose, and finally 5.5 kg of sodium silicate. The mixture was stirred evenly and ground to obtain a dispersion slurry.

The dispersion slurry was stirred and aged at 25° C. for 1.5 hours.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas at the beginning of drying was 560° C., and the temperature of the outlet gas at the end of drying was 120° C.

Figure 6:
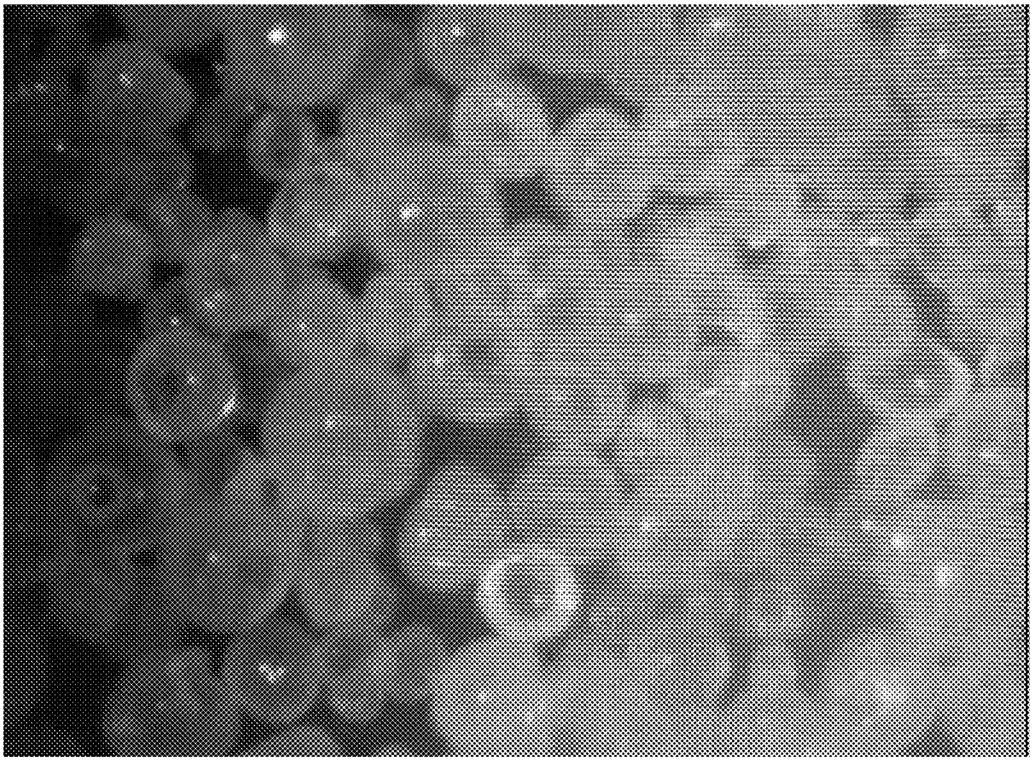
FIG. 6 is a microscopic photo of the microsphere of oxide in the shape of raspberry prepared in the Preparation Example 5.

The microscopic photo of the microspheres of oxide in the shape of raspberry was shown in FIG. 6.

Preparation Example 6

40 kg of water was added into a reaction autoclave. To it, 0.5 kg of aluminum nitrate was added, then 200 g of concentrated sulfuric acid, and then 1 kg of PEG4000 and 5 g picric acid, and finally 3 kg of sodium silicate. The mixture was stirred evenly and ground to obtain a dispersion slurry.

The dispersion slurry was stirred and aged at 25° C. for 1 hour.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas was at the beginning of drying 600° C., and the temperature of the outlet gas at the end of drying was 180° C.

Preparation Example 7

20 L of solution of water and ethanol (with water and ethanol in a volume ratio of 3:1) was added into a reaction autoclave. To it, 1.2 kg of aluminum nitrate was added, then 7 L of concentrated aqua ammonia, and then 2 kg of ethyl cellulose and 7 g of nitroglycerin, and finally 5 kg of TEOS. The mixture was stirred evenly and ground to obtain a dispersion slurry.

The dispersion slurry was stirred and aged at 25° C. for 1.5 hours.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas at the beginning of drying was 700° C., and the temperature of the outlet gas at the end of drying was 160° C.

Preparation Example 8

20 L of solution of water and ethanol (with water and ethanol in a volume ratio of 4:1) was added into a reaction autoclave. To it, 0.3 kg of zircon nitrate was added, then 3 L of concentrated aqua ammonia, and then 0.5 kg of PEG4000 and 6 g of picric acid, and finally 2.6 kg of TEOS. The mixture was stirred evenly and ground to obtain a dispersion slurry.

The dispersion slurry was stirred and aged at 25° C. for 1 hour.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas at the beginning of drying was 660° C., and the temperature of the outlet gas at the end of drying was 140° C.

Preparation Example 9

30 kg of water was added into a reaction autoclave. To it, 1.2 kg of zircon nitrate was added, then 2.5 kg of PEG4000, and finally 7 kg of zirconium hydroxide. The mixture was stirred evenly and ground to obtain a dispersion slurry.

The dispersion slurry was stirred and aged at 45° C. for 1.5 hours.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas at the beginning of drying was 560° C., and the temperature of the outlet gas at the end of drying was 110° C.

Figure 7:
FIG. 7 is a microscopic photo of the microsphere of oxide in the shape of raspberry prepared in the Preparation Example 9.

The microscopic photo of the microspheres of oxide in the shape of raspberry was shown in FIG. 7.

Preparation Example 10

30 kg of water was added into a reaction autoclave. To it, 0.7 kg of zircon nitrate was added, then 2 L of concentrated aqua ammonia, and then 1.5 kg of PEG4000 and 8 g of picric acid, and finally 7 kg of zirconium hydroxide. The mixture was stirred evenly and ground to obtain a dispersion slurry.

The dispersion slurry was stirred and aged at 25° C. for 2 hours.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas at the beginning of drying was 560° C., and the temperature of the outlet gas at the end of drying was 140° C.

Preparation Example 11

30 kg of water was added into a reaction autoclave. To it, 1.2 kg of aluminum nitrate was added, then 2 L of concentrated aqua ammonia, and then 2 kg of PEG4000 and 2 g of trinitrotoluene, and finally 7 kg of zirconium hydroxide. The mixture was stirred evenly and ground to obtain a dispersion slurry.

The dispersion slurry was stirred and aged at 25° C. for 1 hour.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas at the beginning of drying was 620° C., and the temperature of the outlet gas at the end of drying was 141° C.

Preparation Example 12

30 kg of water was added into a reaction autoclave. To it, 0.5 kg of magnesium nitrate was added, then 2.5 L of concentrated aqua ammonia, and then 1 kg of methyl cellulose and 6 g of nitroglycerin, and finally 7.5 kg of zirconium hydroxide. The mixture was stirred evenly and ground to obtain a dispersion slurry.

The dispersion slurry was stirred and aged at 25° C. for 1 hour.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas at the beginning of drying was 560° C., and the temperature of the outlet gas at the end of drying was 140° C.

Preparation Example 13

30 kg of water was added into a reaction autoclave. To it, 1.2 kg of titanium nitrate was added, then 2.5 kg of PEG4000 and 3 g of nitrocellulose, and finally 500 g of concentrated nitric acid and 6 kg of titanium dioxide. The mixture was stirred evenly and ground to obtain a dispersion slurry.

The dispersion slurry was stirred and aged at 55° C. for 1.5 hours.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas at the beginning of drying was 480° C., and the temperature of the outlet gas at the end of drying was 120° C.

Figure 8:
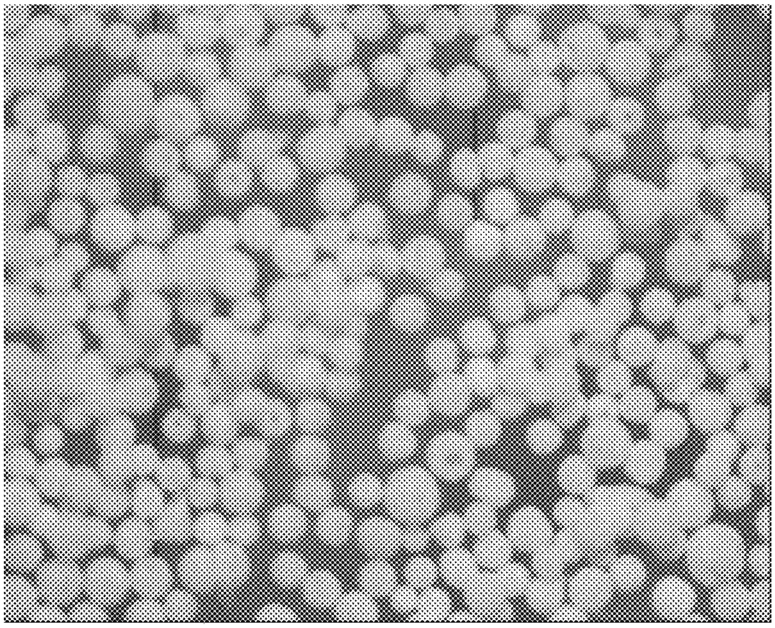
FIG. 8 is a microscopic photo of the microsphere of oxide in the shape of raspberry prepared in the Preparation Example 13.

The microscopic photo of the microspheres of oxide in the shape of raspberry was shown in FIG. 8.

Preparation Example 14

30 kg of water was added into a reaction autoclave. To it, 0.7 kg of titanium nitrate was added, then 2.6 L of concentrated aqua ammonia, and then 1.5 kg of PEG4000 and 6 g of picric acid, and finally 500 g of concentrated nitric acid and 7 kg of titanium nitrate. The mixture was stirred evenly and ground to obtain a dispersion slurry.

The dispersion slurry was stirred and aged at 25° C. for 2 hours.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas at the beginning of drying was 560° C., and the temperature of the outlet gas at the end of drying was 141° C.

Preparation Example 15

30 kg of water was added into a reaction autoclave. To it, 1.2 kg of aluminum nitrate was added, then 2.1 L of concentrated aqua ammonia, and then 2 kg of PEG4000 and 2 g of trinitrotoluene, and finally 400 g of concentrated nitric acid and 7 kg of titanium tetrachloride. The mixture was stirred evenly and ground to obtain a dispersion slurry.

The dispersion slurry was stirred and aged at 25° C. for 1.5 hours.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas at the beginning of drying was 620° C., and the temperature of the outlet gas at the end of drying was 150° C.

Preparation Example 16

30 kg of water was added into a reaction autoclave. To it, 0.5 kg of magnesium nitrate was added, then 2.4 L of concentrated aqua ammonia, and then 1 kg of methyl cellulose and 6 g of nitroglycerin, and finally 400 g of concentrated nitric acid and 7 kg of titanium tetrachloride. The mixture was stirred evenly and ground to obtain a dispersion slurry.

The dispersion slurry was stirred and aged at 25° C. for 1 hour.

The aged dispersion slurry was sent into a spray drying device for shaping by drying, to obtain microspheres of oxide in the shape of raspberry, wherein the atomization pressure of the spray drying was 0.3-3.0 MPa, the pressure in the tower was −0.0010 to −0.0090 MPa, the temperature of the inlet gas at the beginning of drying was 560° C., and the temperature of the outlet gas at the end of drying was 140° C.

Comparative Preparation Example 1

20 kg of water was added into a reaction autoclave. To it, 4.5 kg of pseudo-boehmite powder was added. The mixture was stirred evenly. To it, 200 g of concentrated hydrochloric acid was added. The mixture was ground. To it, 2.3 kg of PEG4000 was added. The mixture was made into a slurry. The slurry was stirred and aged at 25° C. for 1 hour. It was subjected to shaping by drying in a spray drying device, to obtain microspheres of oxide, wherein the atomization pressure of the spray drying was 0.3-3.0 MPa, the pressure in the tower was −0.0010 to −0.0090 MPa, the temperature of the inlet gas at the beginning of drying was 560° C., and the temperature of the outlet gas at the end of drying was 145° C.

Figure 9:
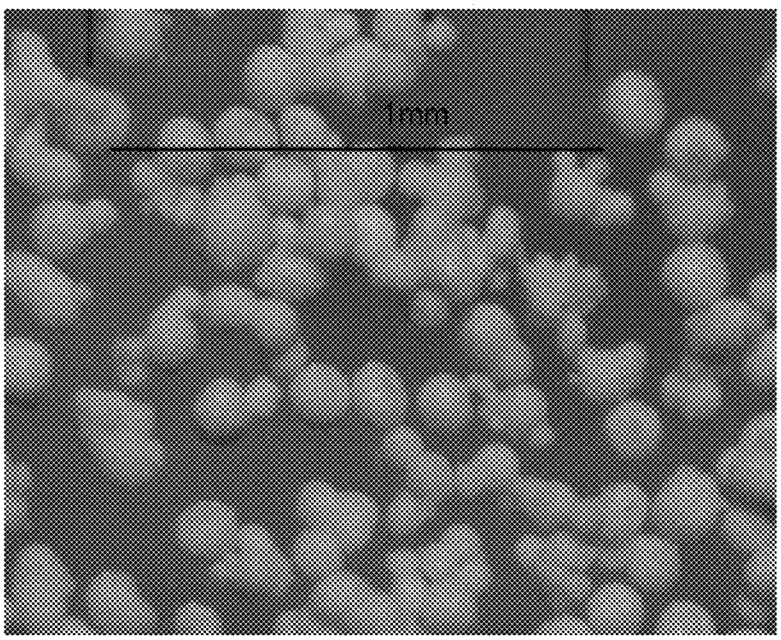
FIG. 9 is a microscopic photo of the microsphere of oxide prepared in the Comparative Preparation Example 1.

The microscopic photo of the obtained microspheres of oxide was shown in FIG. 9. As can be seen, the microspheres were substantially solid, wherein the center part thereof involved seldom hollow structures connected with the outside.

Comparative Preparation Example 2

30 kg of water was added into a reaction autoclave. To it, 5.5 kg of sodium silicate was added. The mixture was stirred evenly. To it, 200 g of concentrated hydrochloric acid was added. The obtained dispersion was filtered. The precipitate was washed twice with ethanol and deionized water respectively, to remove unreacted inorganic and organic impurities.

To it, 20 kg of water and 2.0 kg of PEG4000 was added. The mixture was made into a slurry. The slurry was stirred and aged at 25° C. for 1 hour. It was subjected to shaping by drying in a spray drying device, to obtain microspheres of oxide, wherein the atomization pressure of the spray drying was 0.3-3.0 MPa, the pressure in the tower was −0.0010 to −0.0090 MPa, the temperature of the inlet gas at the beginning of drying was 450° C., and the temperature of the outlet gas at the end of drying was 120° C.

When observed under a microscope, the product had a structure similar to that of the comparative preparation example 1. That is, it was substantially solid, wherein the center part thereof involved seldom hollow structures connected with the outside.

Comparative Preparation Example 3

30 kg of water was added into a reaction autoclave. To it, 7 kg of zircon hydroxide was added. The mixture was stirred vigorously at 30° C. until the materials were fully mixed. The dispersion was ground by a grinder for 30 minutes.

After the mixing and grinding, concentrated aqua ammonia was added as a regulator until the pH value was about 10. After reacting for 2 h, a dispersion was obtained. The dispersion was stirred and aged at 25° C. for 1 hour. It was subjected to shaping by drying in a spray drying device, to obtain microspheres of oxide, wherein the atomization pressure of the spray drying was 0.3-3.0 MPa, the pressure in the tower was −0.0010 to −0.0090 MPa, the temperature of the inlet gas at the beginning of drying was 650° C., and the temperature of the outlet gas at the end of drying was 150° C.

When observed under a microscope, the product had a structure similar to that of the comparative preparation example 1. That is, it was substantially solid, wherein the center part thereof involved seldom hollow structures connected with the outside.

Comparative Preparation Example 4

30 kg of water was added into a reaction autoclave. To it, 6 kg of titanium dioxide and 500 g of concentrated hydrochloric acid were added. The mixture was stirred vigorously at 30° C. until the materials were fully mixed. The obtained dispersion was ground by a grinder for 30 minutes.

After the mixing, reacting and grinding, concentrated aqua ammonia was added as a regulator until the pH value was about 9. After reacting for 2 h, adding 2.5 kg of PEG 4000, a dispersion was obtained. The dispersion was stirred and aged at 45° C. for 1 hour. It was subjected to shaping by drying in a spray drying device, to obtain microspheres of oxide, wherein the atomization pressure of the spray drying was 0.3-3.0 MPa, the pressure in the tower was −0.0010 to −0.0090 MPa, the temperature of the inlet gas at the beginning of drying was 520° C., and the temperature of the outlet gas at the end of drying was 170° C.

When observed under a microscope, the product had a structure similar to that of the comparative preparation example 1. That is, it was substantially solid, wherein the center part thereof involved seldom hollow structures connected with the outside.

Comparative Preparation Example 5

5.5 kg of HZSM-5 molecular sieve with a crystalline size of 300-350 nm, 3 kg of kaolin, 1 kg of cement and 0.5 kg of ammonium carbonate were added into 20 kg deionized water. The mixture was subjected to shear emulsification at 2000 rpm for 2 hours with a homogenizing emulsifier, to form a uniform colloidal slurry with solid content of 31.7%.

300 g of P123 surfactant was added to the colloidal slurry and subjected to further stirring for 1 h, to obtain a slurry of microspheres.

The slurry of microspheres was sent into a spray drying device, wherein the atomization pressure of the spray drying device was 2.8 MPa, the temperature of the inlet of the spray drying device was 280° C., and the temperature of the outlet was 120° C. When flowed out from the outlet of the spray drying device after a time of 2-5 s, microsphere particles were obtained.

Comparative Preparation Example 6

5.5 kg of HZSM-5 molecular sieve with a crystalline size of 300-350 nm, 3 kg of kaolin, 1 kg of cement and 0.5 kg of ammonium carbonate were added into 20 kg deionized water. The mixture was subjected to shear emulsification at 2000 rpm for 2 hours with a homogenizing emulsifier, to form a uniform colloidal slurry with solid content of 31.7%.

300 g of P123 surfactant was added to the colloidal slurry and subjected to further stirring for 1 h, to obtain a slurry of microspheres.

The slurry of microspheres was sent into a spray drying device, wherein the atomization pressure of the spray drying device was 2.8 MPa, the temperature of the inlet of the spray drying device was 560° C., and the temperature of the outlet was 140° C. When flowed out from the outlet of the spray drying device after a time of 2-5 s, microsphere particles were obtained.

Figure 10:
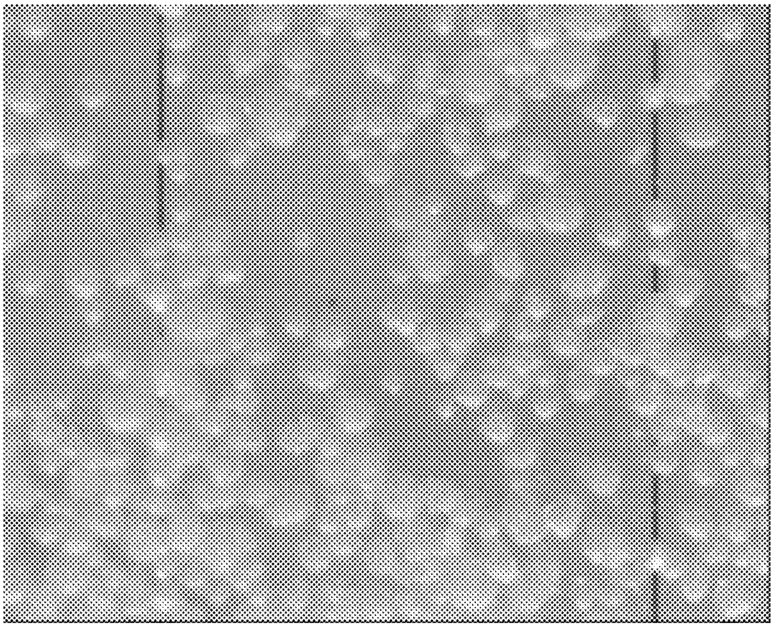
FIG. 10 is a microscopic photo of the microsphere of oxide prepared in the Comparative Preparation Example 6.

The microscopic photo of the obtained microsphere particles was shown in FIG. 10. As can be seen, most of the microsphere particles were in irregular shape. In addition, the center part thereof involved seldom hollow structures connected with the outside.

Comparative Preparation Example 7

5.5 kg of pseudo-boehmite powder, 3 kg of kaolin, 1 kg of cement and 0.5 kg of ammonium carbonate were added into 20 kg deionized water. The mixture was subjected to shear emulsification at 2000 rpm for 2 hours with a homogenizing emulsifier, to form a uniform colloidal slurry with solid content of 31.7%.

300 g of P123 surfactant was added to the colloidal slurry and subjected to further stirring for 1 h, to obtain a slurry of microspheres.

The slurry of microspheres was sent into a spray drying device, wherein the atomization pressure of the spray drying device was 2.8 MPa, the temperature of the inlet of the spray drying device was 280° C., and the temperature of the outlet was 120° C. When flowed out from the outlet of the spray drying device after a time of 2-5 s, microsphere particles were obtained.

Figure 11:
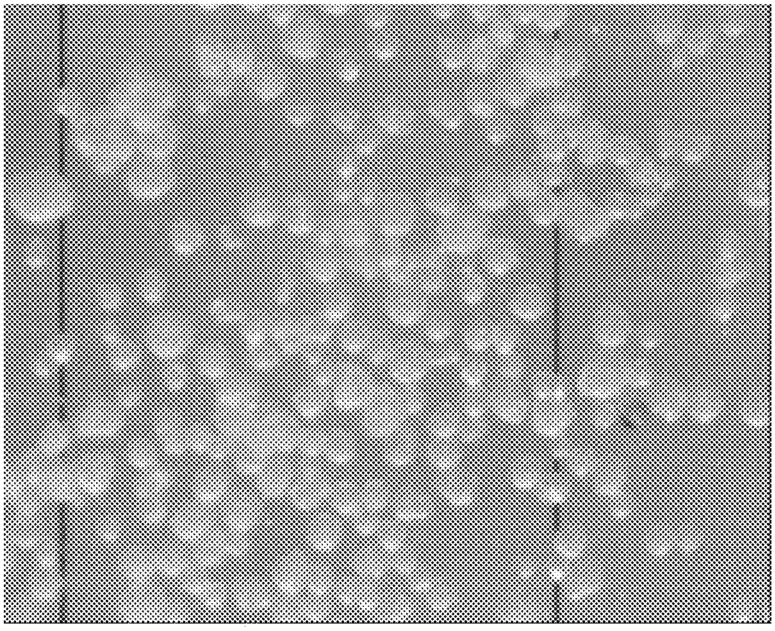
FIG. 11 is a microscopic photo of the microsphere of oxide prepared in the Comparative Preparation Example 7.

The microscopic photo of the obtained microsphere particles was shown in FIG. 11. As can be seen, the microsphere particles were substantially solids, and the center part thereof involved seldom hollow structures connected with the outside.

Working Examples

The following working examples were used to test the effects of using the microspheres of oxide obtained in the preparation examples and comparative preparation examples as supports on catalytic performance.

Working Example 1

The microspheres of oxide in the shape of raspberry obtained in the Preparation Example 1 were calcined at 600° C., to obtain a support ZT1. The physical properties thereof were shown in Table 1.

The support ZT1 was impregnated with a cobalt nitrate solution to prepare a catalyst with a Co content of 16.0%, dried at a temperature of 120° C., and calcined at 420° C. to obtain a catalyst CAT1. The physical properties thereof were shown in Table 2.

Figure 12:
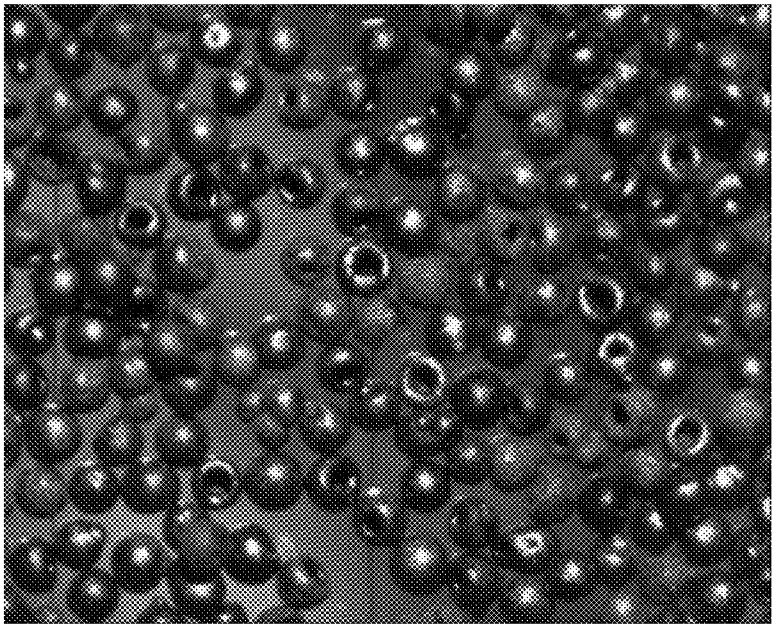
FIG. 12 is a microscopic photo of the catalyst prepared in the Working Example 1.

The microscopic photo of the microspheres of the catalyst CAT1 was shown in FIG. 12.

Working Example 2

The microspheres of oxide in the shape of raspberry obtained in the Preparation Example 2 were calcined at 500° C., to obtain a support ZT2. The physical properties thereof were shown in Table 1.

The support ZT2 was impregnated with a cobalt nitrate solution to prepare a catalyst with a Co content of 16.0%, dried at a temperature of 110° C., and calcined at 350° C. to obtain a catalyst CAT2. The physical properties thereof were shown in Table 2.

Working Example 3

The microspheres of oxide in the shape of raspberry obtained in the Preparation Example 3 were calcined at 500° C., to obtain a support ZT3. The physical properties thereof were shown in Table 1.

The support ZT3 was impregnated with a ferric nitrate solution to prepare a catalyst with a Fe content of 15.0%, dried at a temperature of 120° C., and calcined at 420° C. to obtain a catalyst CAT3. The physical properties thereof were shown in Table 2.

Working Example 4

The microspheres of oxide in the shape of raspberry obtained in the Preparation Example 4 were calcined at 700° C., to obtain a support ZT4. The physical properties thereof were shown in Table 1.

The support ZT4 was impregnated with a ferric nitrate solution to prepare a catalyst with a Fe content of 15.0%, dried at a temperature of 130° C., and calcined at 370° C. to obtain a catalyst CAT4. The physical properties thereof were shown in Table 2.

Working Example 5

The support ZT3 was impregnated with a nitrosylruthenium nitrate solution to prepare a catalyst with a Ru content of 3.0%, dried at a temperature of 120° C., and calcined at 420° C. to obtain a catalyst CAT5. The physical properties thereof were shown in Table 2.

Figure 13:
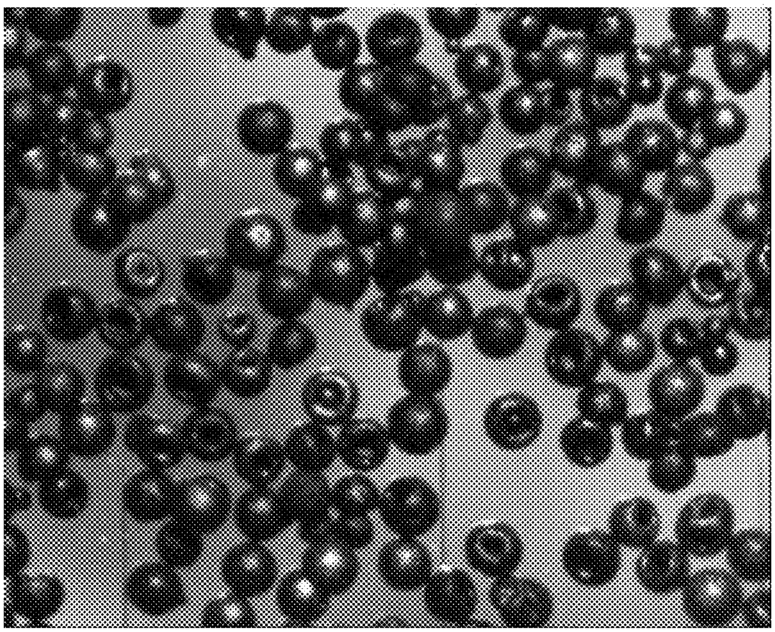
FIG. 13 is a microscopic photo of the catalyst prepared in the Working Example 5.
Figure 14:
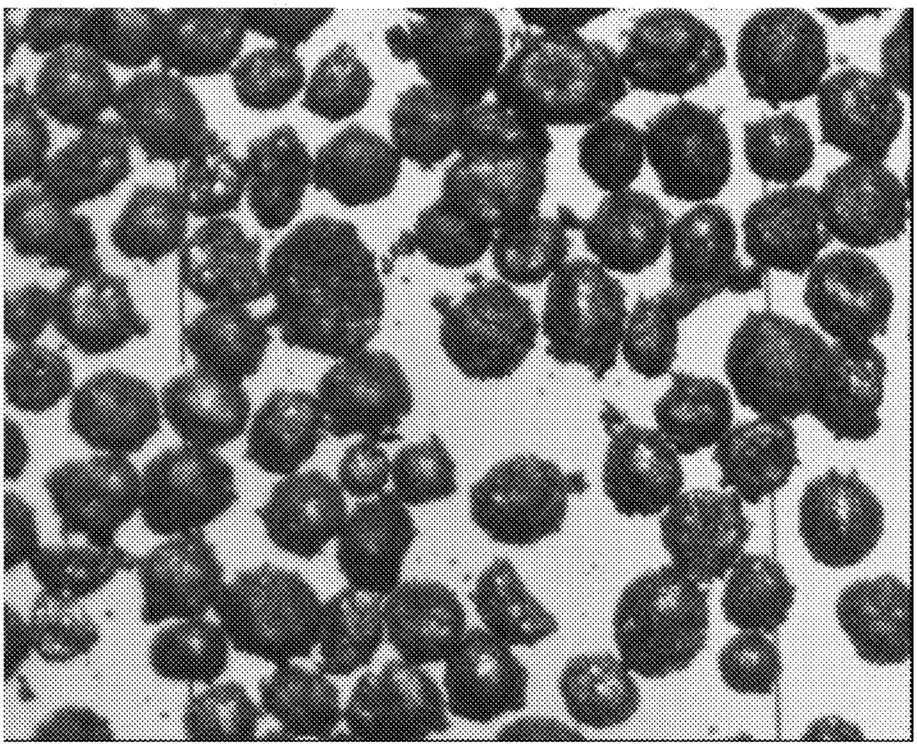
FIG. 14 is a microscopic photo of the catalyst prepared in the Comparative Working Example 1.

The microscopic photo of the microspheres of the catalyst CAT5 was shown in FIG. 13.

Working Example 6

The support ZT4 was impregnated with a nitrosylruthenium nitrate solution to prepare a catalyst with a Ru content of 3.0%, dried at a temperature of 130° C., and calcined at 380° C. to obtain a catalyst CAT6. The physical properties thereof were shown in Table 2.

Working Example 7

The microspheres of oxide in the shape of raspberry obtained in the Preparation Example 5 were calcined at 600° C., to obtain a support ZT5. The physical properties thereof were shown in Table 1.

The support ZT5 was impregnated with a cobalt nitrate solution to prepare a catalyst with a Co content of 16.0%, dried at a temperature of 120° C., and calcined at 420° C. to obtain a catalyst CAT7. The physical properties thereof were shown in Table 2.

Working Example 8

The microspheres of oxide in the shape of raspberry obtained in the Preparation Example 6 were calcined at 500° C., to obtain a support ZT6. The physical properties thereof were shown in Table 1.

The support ZT6 was impregnated with a cobalt nitrate solution to prepare a catalyst with a Co content of 16.0%, dried at a temperature of 110° C., and calcined at 350° C. to obtain a catalyst CAT5. The physical properties thereof were shown in Table 2.

Working Example 9

The microspheres of oxide in the shape of raspberry obtained in the Preparation Example 7 were calcined at 500° C., to obtain a support ZT7. The physical properties thereof were shown in Table 1.

The support ZT7 was impregnated with a ferric nitrate solution to prepare a catalyst with a Fe content of 15.0%, dried at a temperature of 120° C., and calcined at 420° C. to obtain a catalyst CAT5. The physical properties thereof were shown in Table 2.

Working Example 10

The microspheres of oxide in the shape of raspberry obtained in the Preparation Example 8 were calcined at 700° C., to obtain a support ZT8. The physical properties thereof were shown in Table 1.

The support ZT8 was impregnated with a ferric nitrate solution to prepare a catalyst with a Fe content of 15.0%, dried at a temperature of 130° C., and calcined at 370° C. to obtain a catalyst CAT10. The physical properties thereof were shown in Table 2.

Working Example 11

The support ZT7 was impregnated with a nitrosylruthenium nitrate solution to prepare a catalyst with a Ru content of 3.0%, dried at a temperature of 120° C., and calcined at 420° C. to obtain a catalyst CAT11. The physical properties thereof were shown in Table 2.

Working Example 12

The support ZT8 was impregnated with a nitrosylruthenium nitrate solution to prepare a catalyst with a Ru content of 3.0%, dried at a temperature of 130° C., and calcined at 380° C. to obtain a catalyst CAT12. The physical properties thereof were shown in Table 2.

Working Example 13

The microspheres of oxide obtained in the Preparation Example 9 were calcined at 600° C. for 3 hours, to obtain a support ZT13. The physical properties thereof were shown in Table 1.

Working Example 14

The microspheres of oxide obtained in the Preparation Example 13 were calcined at 600° C. for 3 hours, to obtain a support ZT14. The physical properties thereof were shown in Table 1.

Comparative Working Example 1

The microspheres of oxide obtained in the Comparative Preparation Example 1 were calcined at 600° C. for 3 hours, to obtain a support DBZT1. The physical properties thereof were shown in Table 1.

The support DBZT1 was impregnated with a cobalt nitrate solution to prepare a catalyst with a Co content of 16.0%, dried at a temperature of 120° C., and calcined at 420° C. to obtain a catalyst DBCAT-Co-1. The physical properties thereof were shown in Table 2. The microscopic photo of the microspheres of the catalyst DBCAT-Co-1 was shown in FIG. 15.

The support DBZT1 was impregnated with a ferric nitrate solution to prepare a catalyst with a Fe content of 15.0%, dried at a temperature of 120° C., and calcined at 420° C. to obtain a catalyst DBCAT-Fe-1. The physical properties thereof were shown in Table 2.

The support DBZT1 was impregnated with a nitrosylruthenium nitrate solution to prepare a catalyst with a Ru content of 3.0%, dried at a temperature of 120° C., and calcined at 420° C. to obtain a catalyst DBCAT-Ru-1. The physical properties thereof were shown in Table 2.

Comparative Working Example 2

The microspheres of oxide obtained in the Comparative Preparation Example 2 were calcined at 600° C. for 3 hours, to obtain a support DBZT2. The physical properties thereof were shown in Table 1.

The support DBZT2 was impregnated with a cobalt nitrate solution to prepare a catalyst with a Co content of 16.0%, dried at a temperature of 120° C., and calcined at 420° C. to obtain a catalyst DBCAT-Co-2. The physical properties thereof were shown in Table 2.

The support DBZT2 was impregnated with a ferric nitrate solution to prepare a catalyst with a Fe content of 15.0%, dried at a temperature of 120° C., and calcined at 420° C. to obtain a catalyst DBCAT-Fe-2. The physical properties thereof were shown in Table 2.

The support DBZT2 was impregnated with a nitrosylruthenium nitrate solution to prepare a catalyst with a Ru content of 3.0%, dried at a temperature of 120° C., and calcined at 420° C. to obtain a catalyst DBCAT-Ru-2. The physical properties thereof were shown in Table 2.

Comparative Working Example 3

The microspheres of oxide obtained in the Comparative Preparation Example 3 were calcined at 600° C. for 3 hours, to obtain a support DBZT3. The physical properties thereof were shown in Table 1.

Comparative Working Example 4

The microspheres of oxide obtained in the Comparative Preparation Example 4 were calcined at 600° C. for 3 hours, to obtain a support DBZT4. The physical properties thereof were shown in Table 1.

Comparative Working Example 5

The microspheres of oxide obtained in the Comparative Preparation Example 5 were calcined at 600° C. for 3 hours, to obtain a support DBZT5. The physical properties thereof were shown in Table 1.

TABLE 1 physical properties of supports

| support number | specific surface area, $m^2/g$ | pore volume, ml/g | average pore size, nm | crushing rate (strength) | sphericity |
|---|---|---|---|---|---|
| ZT1 | 225 | 0.71 | 8.5 | 0.24% | 0.96 |
| ZT2 | 232 | 0.74 | 7.8 | 0.18% | — |
| ZT3 | 241 | 0.75 | 7.9 | 0.32% | — |
| ZT4 | 214 | 0.68 | 9.1 | 0.27% | — |
| ZT5 | 266 | 0.70 | 7.3 | 0.31% | — |
| ZT6 | 258 | 0.72 | 7.2 | 0.45% | — |
| ZT7 | 275 | 0.71 | 7.4 | 0.32% | 0.94 |
| ZT8 | 274 | 0.70 | 7.3 | 0.51% | — |
| ZT13 | 108 | 0.52 | 7.0 | 0.42% | 0.93 |
| ZT14 | 134 | 0.56 | 6.7 | 0.41% | 0.94 |
| DBZT1 | 221 | 0.70 | 8.4 | 25.0% | 0.74 |
| DBZT2 | 265 | 0.69 | 7.4 | 29.3% | 0.67 |
| DBZT3 | 106 | 0.52 | 7.2 | 30.5% | — |
| DBZT4 | 135 | 0.54 | 6.9 | 28.9% | — |
| DBZT5 | — | — | — | 37.2% | — |

As could be seen from Table 1, when used as supports, the microspheres of oxide in the shape of raspberry obtained in the preparation examples in accordance with the present disclosure had the specific surface area, pore volume and average pore size similar to those of the microspheres of oxide obtained in the comparative preparation examples. However, they achieved substantial improvements on sphericity and strength, which were significantly better than those of the microspheres of oxide obtained in the comparative preparation examples.

TABLE 2 physical properties of catalysts

| catalyst number | specific surface area, $m^2/g$ | pore volume, ml/g | average pore size, nm |
|---|---|---|---|
| CAT1 | 180 | 0.59 | 8.4 |
| CAT2 | 186 | 0.63 | 7.8 |
| CAT3 | 182 | 0.60 | 8.3 |
| CAT4 | 187 | 0.63 | 7.9 |
| CAT5 | 212 | 0.68 | 8.4 |
| CAT6 | 214 | 0.69 | 8.5 |
| CAT7 | 220 | 0.61 | 8.3 |
| CAT8 | 218 | 0.60 | 8.0 |
| CAT9 | 219 | 0.61 | 8.2 |
| CAT10 | 220 | 0.62 | 8.0 |
| CAT11 | 258 | 0.70 | 8.3 |
| CAT12 | 261 | 0.69 | 8.5 |
| DBCAT-Co-1 | 171 | 0.57 | 8.2 |
| DBCAT-Fe-1 | 174 | 0.58 | 8.2 |
| DBCAT-Ru-1 | 211 | 0.68 | 8.4 |
| DBCAT-Co-2 | 213 | 0.60 | 8.1 |
| DBCAT-Fe-2 | 215 | 0.60 | 8.1 |
| DBCAT-Ru-2 | 259 | 0.68 | 8.4 |

The catalysts of the Working Examples 1-12 and the Comparative Working Examples 1-2 were evaluated with respect to their performances in FT synthesis reaction in a fixed bed reactor as described above. Before the FT synthesis catalysts were used, the catalysts were reduced to elemental metals. The conditions for reducing the catalysts included: a normal pressure, a heating rate of 5° C./min, a hydrogen space velocity of 600 $h^{-1}$, a temperature of 400° C., and for a time of 5 hours.

After the reduction, the reaction performance was tested under the following conditions.

The reaction conditions for the cobalt-based catalysts included: raw gas composition of $H_2/CO/N_2$=45%/45%/10% (by volume), a pressure of 2.5 MPa, a temperature of 200° C., 210° C. and 220° C. respectively, and a space velocity of synthesis gas (raw gas) of 24000 $h^{-1}$. The reaction was operated at each reaction temperature for 12 hours, then a gas sample was taken for chromatographic analysis. The main indicators for reaction performance included: conversion of CO, selectivity to methane and selectivity to C5+ hydrocarbons.

The reaction conditions for the iron-based catalysts included: raw gas composition of $H_2/CO/N_2$=45%/45%/10% (by volume), a pressure of 2.5 MPa, a temperature of 260° C., 270° C. and 280° C. respectively, and a space velocity of synthesis gas (raw gas) of 15000 $h^{-1}$. The reaction was operated at each reaction temperature for 12 hours, then a gas sample was taken for chromatographic analysis. The main indicators for reaction performance included: conversion of CO, selectivity to methane, selectivity to C5+ hydrocarbons and selectivity to $CO_2$.

The reaction conditions for the ruthenium-based catalysts included: raw gas composition of $H_2/CO/N_2$=45%/45%/10% (by volume), a pressure of 2.5 MPa, a temperature of 200° C., 210° C. and 220° C. respectively, and a space velocity of synthesis gas (raw gas) of 15000 $h^{-1}$. The reaction was operated at each reaction temperature for 12 hours, then a gas sample was taken for chromatographic analysis. The main indicators for reaction performance included: conversion of CO, selectivity to methane and selectivity to C5+ hydrocarbons.

The results of the test for the reaction performance were shown in Table 3.

TABLE 3 results of the test for the reaction performance of the catalysts

| catalyst number | temperature, ° C. | conversion of CO, % | selectivity to methane, % | selectivity to C5+ hydrocarbons, % | selectivity to $CO_2$, % |
|---|---|---|---|---|---|
| CAT1 | 200 | 22.4 | 4.6 | 88.4 | — |
| | 210 | 29.0 | 5.7 | 86.5 | — |
| | 220 | 37.1 | 6.7 | 84.2 | — |
| CAT2 | 200 | 24.0 | 4.5 | 88.6 | — |
| | 210 | 30.5 | 5.6 | 86.5 | — |
| | 220 | 38.6 | 6.5 | 84.4 | — |
| CAT3 | 260 | 30.3 | 6.9 | 70.2 | 9.6 |
| | 270 | 38.7 | 9.4 | 65.6 | 12.0 |
| | 280 | 47.9 | 13.3 | 59.8 | 14.6 |
| CAT4 | 260 | 30.9 | 5.8 | 71.2 | 8.4 |
| | 270 | 39.6 | 9.0 | 66.0 | 11.8 |
| | 280 | 50.7 | 12.9 | 58.7 | 14.7 |
| CAT5 | 200 | 19.7 | 0.94 | 95.1 | — |
| | 210 | 26.8 | 1.56 | 94.2 | — |
| | 220 | 35.0 | 2.21 | 93.0 | — |
| CAT6 | 200 | 20.1 | 0.89 | 96.1 | — |
| | 210 | 27.9 | 1.45 | 94.7 | — |
| | 220 | 38.1 | 2.16 | 93.6 | — |
| CAT7 | 200 | 18.4 | 6.3 | 89.2 | — |
| | 210 | 25.9 | 7.2 | 88.1 | — |
| | 220 | 35.0 | 9.1 | 86.7 | — |
| CAT8 | 200 | 18.7 | 6.2 | 89.7 | — |
| | 210 | 26.2 | 7.3 | 87.9 | — |
| | 220 | 35.9 | 9.2 | 87.0 | — |
| CAT9 | 260 | 28.3 | 7.8 | 74.2 | 9.3 |
| | 270 | 32.6 | 8.6 | 68.6 | 11.6 |
| | 280 | 38.5 | 12.0 | 66.8 | 13.0 |
| CAT10 | 260 | 29.0 | 7.0 | 76.2 | 8.7 |
| | 270 | 34.0 | 8.3 | 70.0 | 11.4 |
| | 280 | 39.6 | 11.8 | 67.8 | 13.3 |
| CAT11 | 200 | 25.3 | 1.4 | 93.2 | — |
| | 210 | 32.0 | 2.0 | 91.3 | — |
| | 220 | 39.1 | 2.5 | 89.5 | — |
| CAT12 | 200 | 25.0 | 1.2 | 94.0 | — |
| | 210 | 32.1 | 1.8 | 91.5 | — |
| | 220 | 39.4 | 2.3 | 90.2 | — |
| DBCAT-Co-1 | 200 | 17.6 | 5.7 | 87.1 | — |
| | 210 | 25.4 | 7.2 | 82.0 | — |
| | 220 | 35.2 | 11.6 | 78.3 | — |
| DBCAT-Fe-1 | 260 | 27.0 | 12.9 | 60.1 | 10.4 |
| | 270 | 36.7 | 14.5 | 54.2 | 13.6 |
| | 280 | 46.8 | 16.3 | 47.1 | 19.1 |
| DBCAT-Ru-1 | 200 | 17.6 | 1.45 | 91.0 | — |
| | 210 | 23.4 | 2.39 | 89.2 | — |
| | 220 | 30.9 | 4.38 | 88.1 | — |
| DBCAT-Co-2 | 200 | 16.5 | 7.6 | 84.5 | — |
| | 210 | 24.3 | 9.5 | 82.1 | — |
| | 220 | 33.1 | 14.3 | 78.2 | — |
| DBCAT-Fe-2 | 260 | 23.4 | 12.1 | 60.4 | 10.2 |
| | 270 | 28.6 | 16.4 | 54.9 | 14.6 |
| | 280 | 35.4 | 20.0 | 47.8 | 18.1 |
| DBCAT-Ru-2 | 200 | 18.0 | 2.3 | 89.3 | |
| | 210 | 27.2 | 3.8 | 86.7 | |
| | 220 | 36.9 | 5.2 | 83.4 | |

The test results in Table 3 showed that, the Fischer-Tropsch synthesis catalysts prepared by using the microspheres of oxide in the shape of raspberry in accordance with the present disclosure as supports had better performance in FT synthesis under the same conditions. That is, they achieved higher conversion of CO rate and selectivity to C5+ hydrocarbon, but lower selectivity to methane and selectivity to $CO_2$. Furthermore, the catalysts in accordance with the present disclosure achieved the selectivity to methane which was not significantly increased due to the increase in temperature, which significantly solved the diffusion problem in FT synthesis reaction.

Those skilled in the art should understand that the embodiments described herein are merely illustrative. Various replacing, changing and modifying can be made within the scope of the present disclosure. Therefore, the present disclosure is not limited to the above-mentioned embodiments, but is only limited by the claims.

The invention claimed is:

1. A method for preparing a microsphere of oxide that has an internal cavity that opens at a surface thereof, comprising the steps of:

adding a nitrate, a peptizer, a hole-forming agent, the oxide and/or a precursor thereof, and a blasting agent to a dispersant to obtain a dispersion slurry;

aging the dispersion slurry; and drying and shaping the aged dispersion slurry in a drying device to obtain a plurality of microspheres of oxide, wherein the drying device has an inlet temperature of 560-1200° C. and an outlet temperature of 50-300° C., and the nitrate is one or more selected from the group consisting of aluminum nitrate, zirconium nitrate, and yttrium nitrate, the hole-forming agent is one or more selected from the group consisting of starch, synthetic cellulose, polymeric alcohol, and surfactant, the blasting agent is one or more selected from the group consisting of picric acid, trinitrotoluene, nitroglycerin, nitrocellulose, Dana explosive, hexogen and C4 plastic explosive, and wherein, in the drying device, the nitrate, the hole-forming agent, and the blasting agent undergo an oxidation-reduction reaction that generates gas to form the cavity that opens at the surface of the microsphere of oxide.

2. The method of claim 1, wherein:

the peptizer is one or more selected from the group consisting of hydrochloric acid, sulfuric acid, nitric acid, formic acid, acetic acid, oxalic acid, sodium hydroxide, potassium hydroxide, barium hydroxide, calcium hydroxide, aluminum hydroxide, lithium hydroxide, magnesium hydroxide, zinc hydroxide, copper hydroxide, ferric hydroxide, lead hydroxide, cobalt hydroxide, chromium hydroxide, zirconium hydroxide, nickel hydroxide, ammonium hydroxide, anhydrous sodium carbonate, monohydrate sodium carbonate, heptahydrate sodium carbonate, decahydrate sodium carbonate, sodium bicarbonate, potassium carbonate, potassium bicarbonate, amine compounds, alkali metal salts of alcohols, alkaloids, alkyl metal lithium compounds, salts of hydrochloric acid, salts of sulfuric acid, salts of nitric acid, salts of formic acid, salts of acetic acid, and salts of oxalic acid;

the oxide and/or precursor thereof is one or more selected from the group consisting of aluminum sources, silicon sources, zirconium sources, and titanium sources, wherein the aluminum source is one or more selected from the group consisting of pseudo-boehmite, aluminum alkoxide, aluminum nitrate, aluminum sulfate, aluminum chloride, and sodium metaaluminate, wherein the silicon source is one or more selected from the group consisting of silicate esters, sodium silicate, water glass and silica sol, wherein the zirconium source is one or more selected from the group consisting of zirconium dioxide, zirconium tetrachloride, zirconyl chloride, zirconium hydroxide, zirconium sulfate, zirconium phosphate, zirconyl nitrate, zirconium nitrate, basic zirconium carbonate, and zirconium tetrabutoxide, and wherein the titanium source is one or more selected from the group consisting of titanium dioxide, metatitanic acid, titanium nitrate, titanyl sulfate, titanium dichloride, titanium trichloride, titanium tetrachloride, aluminum titanium chloride, tetraethyl titanate, tetrabutyl titanate, tetra-n-propyl titanate, and tetraisopropyl titanate; and the dispersant is one or more selected from the group consisting of water, alcohols, ketones, and acids.

3. The method of claim 1, wherein a mass ratio of the nitrate, the peptizer, the hole-forming agent and the oxide and/or precursor thereof is (10-500):(1-10):(10-500):(10-1000).

4. The method of claim 1, further comprising adding a blasting agent to the dispersant, wherein the blasting agent is one or more selected from the group consisting of picric acid, trinitrotoluene, nitroglycerin, Dana explosive, hexogen, and C4 plastic explosive, and an amount of the blasting agent is added is less than 1% of a total dry weight of the nitrate, the peptizer, the hole-forming agent, and the oxide and/or precursor thereof.

5. The method of claim 1, wherein the drying device is a flash drying device or a spray drying device.

6. The method of claim 1, wherein the aging is carried out at a temperature of 0-90° C.

7. The microsphere of oxide prepared by the method of claim 1, wherein the oxide is one or more selected from the group consisting of alumina, silica, zirconia, magnesium oxide, calcium oxide, and titania.

* * * * *